US005977060A

United States Patent [19]

Zitter et al.

[11] Patent Number: 5,977,060

[45] Date of Patent: Nov. 2, 1999

[54] INSECT CONTROL WITH A HYPERSENSITIVE RESPONSE ELICITOR

[75] Inventors: Thomas A. Zitter, Ithaca, N.Y.; Zhong-Min Wei, Kirkland, Wash.

[73] Assignees: Cornell Research Foundation, Inc., Ithaca, N.Y.; EDEN Bioscience, Bothell, Wash.

[21] Appl. No.: 09/030,270

[22] Filed: Feb. 25, 1998

Related U.S. Application Data

[60] Provisional application No. 60/039,226, Feb. 28, 1997.

[51] Int. Cl.$^6$ .................................................... A01N 37/18

[52] U.S. Cl. ............................ 514/2; 530/350; 536/23.7; 536/23.74

[58] Field of Search ................................ 514/2; 530/350; 536/23.1, 23.7, 23.74

[56] References Cited

U.S. PATENT DOCUMENTS

| | | | |
|---|---|---|---|
| 4,569,841 | 2/1986 | Liu | 424/93.4 |
| 4,597,972 | 7/1986 | Taylor | 426/36 |
| 4,601,842 | 7/1986 | Caple et al. | 252/70 |
| 4,740,593 | 4/1988 | Gonzalez et al. | 175/421 |
| 4,851,223 | 7/1989 | Sampson | 424/711 |
| 4,886,825 | 12/1989 | Ruess et al. | 514/383 |
| 4,931,581 | 6/1990 | Schurter et al. | 560/18 |
| 5,057,422 | 10/1991 | Bol et al. | 800/298 |
| 5,061,490 | 10/1991 | Paau et al. | 424/93.47 |
| 5,135,910 | 8/1992 | Blackburn et al. | 514/2 |
| 5,173,403 | 12/1992 | Tang | 435/6 |
| 5,217,950 | 6/1993 | Blackburn et al. | 514/2 |
| 5,243,038 | 9/1993 | Ferrari et al. | 536/23.1 |
| 5,244,658 | 9/1993 | Parke | 504/117 |
| 5,260,271 | 11/1993 | Blackburn et al. | 514/2 |
| 5,348,743 | 9/1994 | Ryals et al. | 424/94.61 |
| 5,494,684 | 2/1996 | Cohen | 424/523 |
| 5,523,311 | 6/1996 | Schurter et al. | 514/361 |
| 5,550,228 | 8/1996 | Godiard et al. | 800/298 |
| 5,552,527 | 9/1996 | Godiard et al. | 514/398 |
| 5,650,387 | 7/1997 | Wei et al. | 514/2 |
| 5,708,139 | 1/1998 | Collmer et al. | 530/350 |

FOREIGN PATENT DOCUMENTS

| | | |
|---|---|---|
| WO 94/01546 | 1/1994 | WIPO . |
| WO 94/26782 | 11/1994 | WIPO . |
| WO 95/19443 | 7/1995 | WIPO . |
| WO 96/39802 | 12/1996 | WIPO . |

OTHER PUBLICATIONS

Inbar et al., "Elicitors of Plant Defensive Systems Reduce Insect Densities and Disease Incidence," *Journal of Chemical Ecology,* 24(1): 135–149 (1998).

Jin et al., "A Truncated Fragment of Harpin$_{Pss}$ Induces Systemic Resistance to *Xanthomonas campestris* pv. Oryzae in Rice," *Physiological and Molecular Plant Pathology,* 51:243–257 (1997).

Frederick et al., "The WTS Water–Soaking Genes of *Erwinia stewartii* are Related to hrp Genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. *glycines*," Seventh International Symposium on Molecular Plant Microbe Interactions, Abstract No. 244 (Jun. 1994).

Preston et al., "The HrpZ Proteins of *Pseudomonas syringae* pvs. *syringae, glycinea*, and tomato are Encoded by an Operon Containing Yersinia ysc Homologs and Elicit the Hypersensitive Response in Tomato but not Soybean," *Mol. Plant–Microbe Interact.,* 8(5):717–32 (1995).

Bauer et al., "*Erwinia chrysanthemi* hrp Genes and their Involvement in Elicitation of the Hypersensitive Response in Tobacco," Sixth International Symposium on Molecular Plant Microbe Interactions, Abstract No. 146 (Jul. 1992).

Stryer, L., "Enzymes are Highly Specific," *Biochemistry,* San Francisco: W.H. Freeman and Company, p. 116 (1975).

Keen et al., "Inhibition of the Hypersensitive Reaction of Soybean Leaves to Incompatible *Pseudomonas spp.* by Blasticidin S, Streptomycin or Elevated Temperature," *Physiological Plant Pathology,* 18:325–37 (1981).

Lerner, R.A., "Tapping the Immunological Repertoire to Produce Antibodies of Predetermined Specificity," *Nature,* 299:592–96 (1982).

Staskawicz et al., "Cloned Avirulence Gene of *Pseudomonas Syringae* pv. *glycinea* Determines Race–specific Incompatiblity on Glycine max (L.) Merr.," *Proc. Natl. Acad. Sci. USA,* 81:6024–28 (1984).

Bauer et al., "*Erwinia chrysanthemi* Harpin$_{Ech}$: An Elicitor of the Hypersensitive Response that Contributes to Soft–Rot Pathogenesis," *MPMI,* 8(4):484–91 (1995).

Huang et al., "Characterization of the hrp Cluster from *Pseudomonas syringae* pv. *syringae* 61 and TnphoA Tagging of Genes Encoding Exported or Membrane–Spanning Hrp Proteins," *Molec. Plant–Microbe Interact.,* 4(5):469–79 (1991).

Huang et al., "The *Pseudomonas syringae* pv. *syringae* 61 hrpH Product, an Envelope Protein Required for Elicitation of the Hypersensitive Response in Plants," *J. Bacteriol.,* 174(21):6878–85 (1992).

Bonas, U., "hrp Genes of Phytopathogenic Bacteria," *Current Topics in Microbio.,* 192:79–98 (1994).

(List continued on next page.)

*Primary Examiner*—Nancy Degen
*Assistant Examiner*—Irem Yucel
*Attorney, Agent, or Firm*—Nixon, Hargrave, Devans & Doyle LLP

[57] ABSTRACT

The present invention relates to a method of controlling insects on plants. This involves applying a hypersensitive response elicitor polypeptide or protein in a non-infectious form to a plant or plant seed under conditions effective to control insects on the plant or plants produced from the plant seed. Alternatively, transgenic plants or transgenic plant seeds transformed with a DNA molecule encoding a hypersensitive response elicitor polypeptide or protein can be provided and the transgenic plants or plants resulting from the transgenic plant seeds are grown under conditions effective to control insects.

49 Claims, 2 Drawing Sheets

OTHER PUBLICATIONS

Arlat et al., "PopA1, A Protein Which Induces a Hypersensitivity–Like Response on Specific Protein Petunia Genotypes, is Secreted via the Hrp Pathway of *Pseudomonas solanacearum*," *The EMBO J.,* 13(3):543–53 (1994).

Kessmann et al., "Induction of Systemic Acquired Disease Resistance in Plants by Chemicals," *Ann. Rev. Phytopathol.,* 32:439–59 (1994).

Kelman, A., "The Relationship of Pathogenicity in *Pseudomonas solanacearum* To Colony Appearance on a Tetrazolium Medium," *Phytopathology,* 44:693–95 (1954).

Winstead et al., "Inoculation Techniques For Evaluating Resistance to *Pseudomonas solanacearum," Phytopathology,* 42:628–34 (1952).

Ahl et al., "Iron Bound–Siderophores, Cyanic Acid, and Antibiotics Involved in Suppression of *Thielaviopsis basiocola* by a *Pseudomonas fluorescens* Strain," *J. Phytopathology,* 116:121–34 (1986).

Anderson et al., "Responses of Bean to Root Colonization with *Pseudomonas putida* in a Hydroponic System," *Phytopathology,* 75(9):992–95 (1985).

Gardner et al., "Growth Promotion and Inhibition by Antibiotic–Producing Fluorescent Pseudomonads on Citrus Roots," *Plant and Soil,* 77:103–13 (1984).

Kloepper,J.W., "Effect of Seed Piece Inoculation with Plant Growth–Promoting Rhizobacteria on Populations of *Erwinia carotovora* on Potato Roots and In Daughter Tubers," *Phytopathology,* 73(2):217–19 (1983).

Atkinson et al., "The Hypersensitive Reaction of Tobacco to *Pseudomonas syringae* pv. pisi," *Plant Physiol.,* 79:843–47 (1985).

Huynh et al., "Bacterial Blight of Soybean: Regulation of a Pathogen Gene Determinig Host Cultivar Specificity," *Science,* 245:1374–77 (1986).

Kloepper et al., "Plant Growth–Promoting Rhizobacteria on Canola (Rapeseed)," *Plant Disease,* 72(1):42–6 (1988).

Kloepper et al., "Enhanced Plant Growth by Siderophores Produced by Plant Growth–Promoting Rhizobacteria," *Nature,* 286:885–86 (1980).

Kloepper et al., "Pseudomonas Siderophores: A Mechanism Explaining Disease–Suppressive Soils," *Current Microbiology,* 4:317–20 (1980).

Kloepper et al., "Emergence–Promoting Rhizobacteria; Description and Implications for Agriculture," In: *Iron, Siderophores, and Plant Disease,* Swinborne (ed), Plenum, NY, 155–64 (1986).

Kloepper et al., "Relationships of in vitro Antibiosis of Plant Growth–Promoting Rhizobacteria to Plant Growth and the Displacement of Root Microflora," *Phytopathology,* 71(10):1020–24 (1981).

Kloepper et al., "Effects of Rhizosphere Colonization by Plant Growth–Promoting Rhizobacteria on Potato Plant Development and Yield," *Phytopathology,* 70(11):1078–82 (1980).

Kloepper et al., "Plant Growth Promotion Mediated by Rhizosphere Bacterial Colonizers," In: *The Rhizosphere and Plant Growth,* –315–32, Keister et al. (eds), pp. 315–326 (1991).

Lifshitz et al., "Growth Promotion of Canola (rapeseed) Seedlings by a Strain of *Pseudomonas putida* Under Gnotobiotic Conditions," Conditions, *Microbiol.* 33:390–95 (1987).

Loper et al., "Influence of Bacterial Sources of Indole–3–acetic Acid on Root Elongation of Sugar Beet," *Phytopathology,* 76(4):386–89 (1986).

Schroth et al., "Disease–Suppressive Soil and Root–Colonizing Bacteria," *Science,* 216:1376–81 (1982).

Stutz et al., "Naturally Occurring Fluorescent Pseudomonads Involved Suprpession of Black Root Rot of Tobacco," *Phytopathology,* 76(2):181–85 (1986).

Lindgren et al., "Gene Cluster of *Pseudomonas syringae* pv. *phaseolicola* Controls Pathogenicity of Bean Plants and Hypersensitivity on Nonhost Plants," *J. Bacteriol.,* 168(2):512–22 (1986).

Bauer et al., "Cloning of a Gene from *Erwinia Amylovora* Involved in Induction of Hypersensitivity and Pathogenicity," *Plant Pathogenic Bacteria,* Proceedings of the Sixth International Conference on Plant Pathogenic Bacteria, Maryland, pp. 425–29 (1987).

Wei et al., "Induction of Systemic Resistance of Cucumber to *Colletotrichum orbiculare* by Select Strains of Plant Growth–Promoting Rhizobacteria," *Phytopathology,* 81:1508–12 (1991).

Wei et al., "Induction of Systemic Resistance with Seed Treatment by PGPR Strains," pp. 191–194.

Weller, D.M., "Biological Control of Soilborne Plant Pathogens in the Rhizosphere with Bacteria," *Ann. Rev. Phytopathol.,* 26:379–407 (1988).

Young et al., "PGPR: Is There a Relationship Between Plant Growth Regulators and the Stimulation of Plant Growth or Biological Activity?," pp. 182–186.

Wei et al., "Induced Systemic Resistance by Select Plant Growth–Promoting Rhizobacteria Against Bacterial Wilt of Cucumber and the Beetle Vectors," *Phytopathology,* 86:1154, Abstract No. 313 (1995).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology,* 118:165–70 (1987).

Malamy et al., "Salicylic Acid: A Likely Endogenous Signal in the Resistance Response of Tobacco to Viral Infection," *Science,* 250:1002–04 (1990).

Cameron et al., "Biologically Induced Systemic Acquired Resistance in *Arabidopsis thaliana*," *The Plant Journal,* 5(5):715–25 (1994).

Laby et al., "Structural and Functional Analysis of *Erwinia amylovora* Harpin, An Elicitor of the Plant Hypersensitive Response," *Phytopathology,* 84:345 (194).

Van Gijsegem et al., "Evolutionary Conservation of Pathogenicity Determinants Among Plant and Animal Pathogenic Bacteria," *Trends Micorbiol.,* 1:175–80 (1993).

Kamoun, et al., "Extracellular Protein Elicitors from Phytophthora: Host–Specificity and Induction of Resistance to Bacterial and Fungal Phytopathogens," *Molecular Plant–Microbe Interactions,* 6(1):15–25 (1993).

Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal,* 8(4):551–60 (1995).

Collinge et al., "Plant Gene Expression in Response to Pathogens," *Plant Molecular Biology,* 9:389–410 (1987).

Shatzman et al., "Expression, Identification, and Characterization of Recombinant Gene Products in *Escherichia coli*, " *Methods in Enzymology,* 152:661–73 (1987).

Tenhaken, et al., "Function of the Oxidative Burst in Hypersensitive Disease Resistance," *Proc. Natl. Acad. Sci. USA,* 92:4158–63 (1995).

Bonnet, et al., "Induction de nécroses foliarires, de protéines b et de résistance dans les interactions tabac Phytophthora," *Agronomic,* 6(9):829–37 (1986).

Gallitelli, et al., "Satellite–Mediated Protection of Tomato Against Cucumber Mosaic Virus: II. Field Test Under Natural Epidemic Conditions in Southern Italy," *Plant Disease,* 75(1):93–5 (1991).

Kang et al., "Control of Tomato Mosaic Disease by Interference of an Attenuated Virus," *Res. Rept. RDA (Hort.),* 27(1):17–26 (1985).

Montasser, et al., "Satellite–Mediated Protection Against Cucumber Mosaic Virus: I. Greenhouse Experiments and Simulated Epidemic Conditions in the Field," *Plant Disease,* 75(1):86–92 (1991).

Marks, R.J., "Varietal Resistance to Potato Cyst Nematode," *Agricultural Entomology,* pp. 63–67 (1979).

Walton, et al., "Host–Selective Toxins and Disease Specificty: Perspectives and Progress," *Annu. Rev. Phytopathol.,* 31:275–303 (1993).

Atkinson, M.M., "Molecular Mechanisms of Pathogen Recognition by Plants," *Advances in Plant Pathology,* 10:36–64 (1993).

Godiard, et al., "Differential Regulation in Tobacco Cell Suspensions of Genes Involved in Plant–Bacteria Interactions by Pathogen–Related Signals," *Plant Molecular Biology,* 17:409–13 (1991).

Ricci, et al., "Structure and Activity of Proteins from Pathogenic Fungi Phytophthora Eliciting Necrosis and Acquired Resistance in Tobacco," *Eur. J. Biochem.,* 183:555–63 (1989).

Lakhmatova, I.T., "Induction of Plant Resistance to Viral Disease: Application of Vaccination," *Sel'skokhozyaistyennaya Biologiya, Biologiya* 3:39–51 (1991).

*Biologicheskii Zhurnal Armenii,* 31(3):305–09 (1978).

Lakhmatova, I.T., "Using Biologically Active Substances to Induced Plant Resistance to Viruses Immunization," *Sel'skokhozyaistvennaya Biologiya,* 3:13–22 (1992).

Shields, R., "Towards Insect–Resistant Plants," *Nature,* 328:12–13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.,* 170(10):4748–50 (1988).

Ricci et al., "Differential Production of Parasiticein, an Elicitor of Necrosis and Resistance in Tobacco, by Isolates of *Phytophthora parasitica*," *Plant Pathology,* 41:298–307 (1992).

Honée, et al., "Molecular Characterization of the Interaction Between the Fungal Pathogen *Cladosporium fulvum* and Tomato," *Advances in Molecular Genetics of Plant–Microbe Interactions,* 3:199–206 (1994).

Keller, et al., "Responses of Tobacco to Elicitins, Proteins From *Phytopthora Spp.* Eliciting Acquired Resistance," *Advances in Molecular Genetics of Plant–Microbe Interactions,* 3:327–32 (1994).

Keen, et al., "Bacteria Expressing Avirulence Gene D Produce a Specific Elicitor of the Soybean Hypersensitive Reaction," *Molecular Plant–Mircobe Interactions,* 3(2):112–21 (1990).

Bauer, et al., "*Erwinia chrysanthemi* hrp Genes and Their Involvement in Soft Rot Pathogenesis and Elicitation of the Hypersensitive Response," *MPMI,* 7(5):573–81 (1994).

Schottens–Toma et al., "Purification and Primary Structure of a Necrosis–inducing Peptide from the Apoplastic Fluids of Tomato Infected with *Cladosporium fulvum* (syn. *Fulvia fulva*)," *Physiological and Molecular Plant Pathology,* 33:59–67 (1988).

Steinberger et al., "Creation and Complementation of Pathogenicity Mutants of *Erwinia amylovora*, " *Molecular Plant–Microbe Interactions,* 1(3):135–44 (1988).

Beer et al., "The Hypersensitive Response is Elicited by *Escherichia coli* Containing a Cluster of Pathogenicity Genes from *Erwinia amylovora*, " *Phytopathology,* 79(10):1156 (Abstract 169) (1989).

Hiatt et al., "Production of Antibodies in Transgenic Plants," *Nature,* 342:76–8 (1989).

Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology,* 50:230–34(1989).

Huang et al., "Isolation and Purification of a Factor from *Pseudomonas solanacearum* That Induces a Hypersensitive––like Response in Potato Cells," *Molecular Plant–Microbe Interactions,* 2(3):132–38 (1989).

James et al., "Genetic Transformation of Apple (*Malus pumila* Mill.) Using a Disarmed Ti–binary Vector," *Plant Cell Reports,* 7:658–61 (1989).

Laby et al., "Cloning and Preliminary Characterization of an hrp Gene Cluster of *Erwinia amylovora*," *Phytopathology,* 79(10):1211 (Abstract 607) (1989).

Dow et al., "Extracellular Proteases from *Xanthomonas campestris* pv. Campestris, the Black Rot Pathogen," *Applied and Environmental Microbiology,* 56(10):2994–98 (1990).

Walters et al., "Gene for Pathogenicity and Ability to Cause the Hypersensitive Reaction Cloned from *Erwinia amylovora*," *Physiological and Molecular Plant Pathology,* 36:509–21 (1990).

Wu et al., "Cloning, Genetic Organization, and Characterization of a Structural Gene Encoding Bacillopeptidase F from *Bacillus subtilis*," *The Journal of Biological Chemistry,* 265(12):6845–50 (1990).

Bauer et al., "Further Characterization of an hrp Gene Cluster of *Erwinia amylovora*," *Molecular Plant–Microbe Interactions,* 4(5):493–99 (1991).

Beer et al., "The hrp Gene Cluster of *Erwinia amylovora*," *Advances in Molecular Genetics of Plant–Microbe Interactions,* 1:53–60 (1991).

Benvenuto et al., "'Phytoantibodies': A General Vector for the Expression of Immunoglobulin Domains in Transgenic Plants," *Plant Molecular Biology,* 17:865–74 (1991).

Milat et al., "Physiological and Structural Changes in Tobacco Leaves Treated with Crytogein, a Proteinaceous Elicitor from *Phyutophthora cryptogea*," *Phytopathology,* 81(11):1364–68 (1991).

Ruberti et al., "A Novel Class of Plant Proteins Containing a Homeodomain with Closely Linked Leucine Zipper Motif," *The EMBO Journal,* 10(7):1787–91 (1991).

Quigley et al., "Nucleotide Sequence and Expression of a Novel Glycine–Rich Protein Gene from *Arabidopsis thaliana*," *Plant Molecular Biology,* 17:949–52 (1991).

van Kan et al., "Cloning and Characterization of cDNA of Avirulence Gene avr9 of the Fungal Pathogen *Cladosporium fulvum*, Causal Agent of Tomato Leaf Mold," *Molecular Plant–Microbe Interactions,* 4(1):52–9 (1991).
Waldmann, T.A., "Monoclonal Antibodies in Diagnosis and Therapy," *Science,* 252:1657–62 (1991).
Willis et al., "hrp Genes of Phytopathogenic Bacteria," *Molecular Plant–Microbe Interactions,* 4(2):132–38 (1991).
Beer et al., "Are Harpins Univerisal Elicitors of the Hypersensitive Response of Phytopathogenic Bacteria?," *Advances in Molecular Genetics of Plant–Microbe Interactions,* 2:281–86 (1992).
Laby et al., "Hybridization and Functional Complementation of the hrp Gene Cluster from *Erwinia amylovora* Strain Ea321 with DNA of Other Bacteria," *Molecular Plant–Microbe Interactions,* 5(5):412–19 (1992).
Sandhu, "Protein Engineering of Antibodies," *Crit. Rev. in Biotech.,* 12(5/6):437–62 (1992).
Wei et al., "Harpin, Elicitor of the Hypersensitive Response Produced by the Plant Pathogen *Erwinia amylovora*, " *Science,* 257:85–8 (1992).
He et al., "*Pseudomonas syringae* pv. *syringae* $Harpin_{Pss}$: A Protein that is Secreted via the Hrp Pathway and Elicits the Hypersensitive Response in Plants," *Cell,* 73:1255–66 (1993).
Bonas, U., "Bacterial Home Goal by Harpins," *Trends in Microbiology,* 2:1–2 (1994).
Boccara, et al., "Plant Defense Elicitor Protein Produced by *Erwinia chrysanthemi*," *Mechanisms of Plant Defense Responses,* p. 166 (1993).
Qui et al., "Treatment of Tomato Seed with Harpin Enhances Germination and Growth and Induces Resistance to *Ralstonia solanacearum*," *Phytopathology,* 87:6, S80 (1997).
Burr et al., "Increased Potato Yields by Treatment of Seedpieces with Specific Strains of *Pseudomonas fluorescens* and *P. putida*," *Phytopathology,* 68:1377–1383 (1978).
Ricci et al., "Proteinaceous Elicitors of Plant Defense Responses," B. Fritig eds., *Mechanisms of Plant Defense Responses,* Netherlands, pp. 121–130 (1993).
Keen et al., "Syringolide Elicitors Specified By Avirulence Gene D Alleles In *Pseudomonas syringae*," *Advances in Molecular Genetics of Plant–Microbe Interactions,* 3:41–48 (1994).
Klessing et al., "The Salicylic Acid Signal In Plants," *Plant Molecular Biology,* 26:1439–1458 (1994).
Bogdanove et al., "Unified Nomenclature For Broadly Conserved hrp Genes of Phytopathogenic Bacteria," *Molecular Microbiology,* 20(3):681–683 (1996).
Bonnet et al., "Acquired Resistance Triggered By Elicitins In Tobacco and Other Plants," *European Journal of Plant Pathology,* 102:181–192 (1996).
Cui et al., "The RsmA Mutants of *Erwinia carotovora* subsp. *carotovora* Strain Ecc71 Overexpress $hrpN_{Ecc}$ and Elicit a Hypersensitive Reaction–like Response in Tobacco Leaves," *Molecular Plant–Microbe Interactions,* 9(7):565–573 (1996).
Gopalan et al., "Bacterial Genes Involved in the Elicitation of Hypersensitvie Response and Pathogenesis," *Plant Disease,* 80(6):604–610 (1996).
Hoffland et al., "Comparison of Systemic Resistance Induced by Avirulent and Nonpathogenic Pseudomonas Species," *Phytopathology,* 86(7):757–762 (1996).
Ryals et al., "Systemic Acquired Resistance," *The Plant Cell,* 8:1809–1819 (1996).
Wei et al., "Induced Systemic Resistance to Cucumber Diseases and Increased Plant Growth by Plant Growth–Promoting Rhizobacteria Under Field Conditions," *Phytopathology,* 86:221–224 (1996).
Wengelnik et al., "Expression and Localization of HrpA1, a Protein of *Xanthomonas campestris* pv. vesicatoria Essential for Pathogenicity and Induction of the Hypersensitivity Reaction," *Journal of Bacteriology,* 178:1061–1069 (1996).

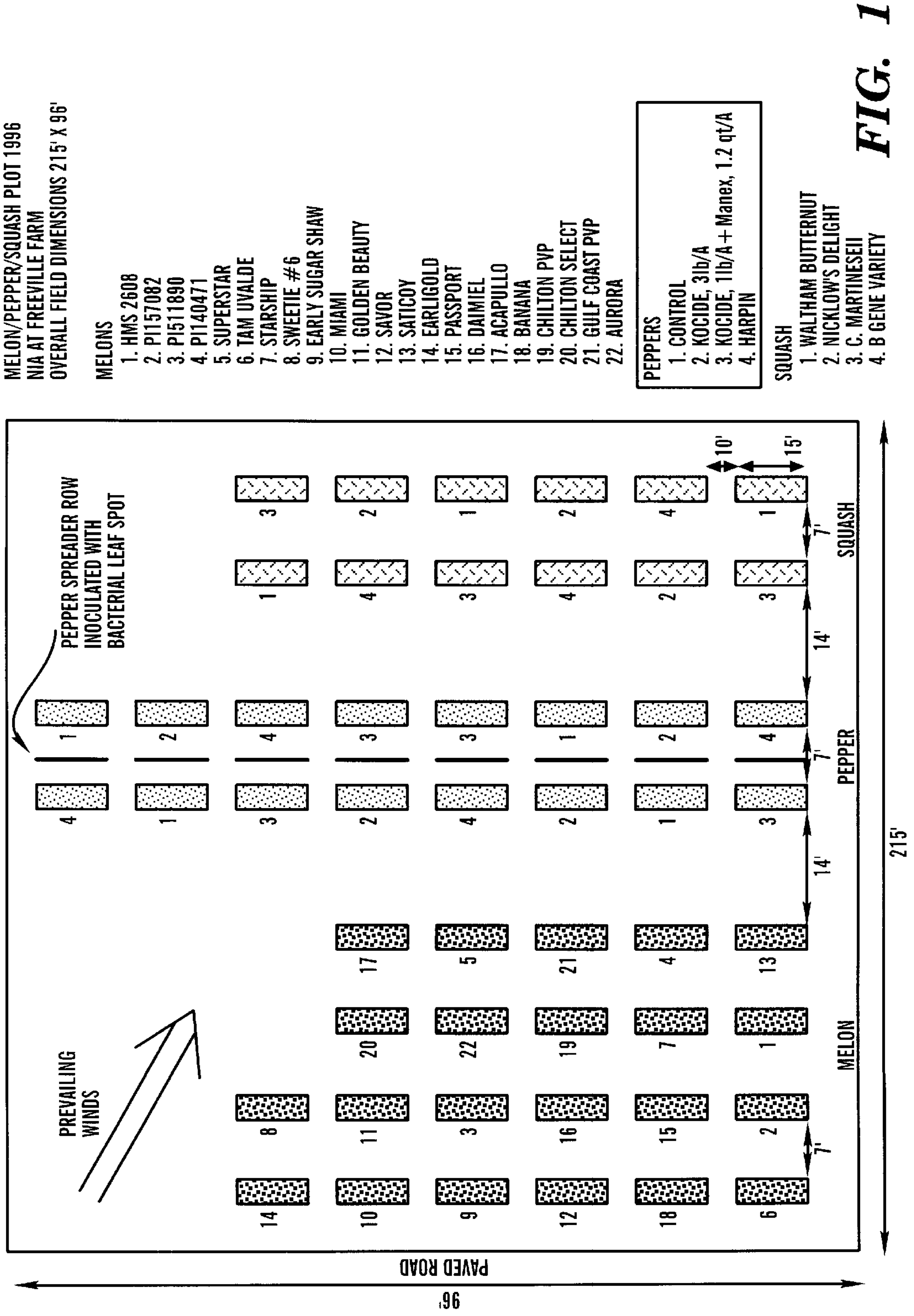

FIG. 1

MELON/PEPPER/SQUASH PLOT 1996
NIA AT FREEVILLE FARM
OVERALL FIELD DIMENSIONS 215' X 95'

MELONS
1. HMS 2608
2. PI157082
3. PI511890
4. PI140471
5. SUPERSTAR
6. TAM UVALDE
7. STARSHIP
8. SWEETIE #6
9. EARLY SUGAR SHAW
10. MIAMI
11. GOLDEN BEAUTY
12. SAVOR
13. SATICOY
14. EARLIGOLD
15. PASSPORT
16. DAIMIEL
17. ACAPULLO
18. BANANA
19. CHILTON PVP
20. CHILTON SELECT
21. GULF COAST PVP
22. AURORA

PEPPERS
1. CONTROL
2. KOCIDE, 3lb/A
3. KOCIDE, 1lb/A + Manex, 1.2 qt/A
4. HARPIN SQUASH
1. WALTHAM BUTTERNUT
2. NICKLOW'S DELIGHT
3. C. MARTINESEII
4. B GENE VARIETY

```
                        SEQUENCE LISTING

(1) GENERAL INFORMATION:

   (iii) NUMBER OF SEQUENCES: 10

(2) INFORMATION FOR SEQ ID NO:1:

     (i) SEQUENCE CHARACTERISTICS:
          (A) LENGTH: 338 amino acids
          (B) TYPE: amino acid
          (C) STRANDEDNESS:
          (D) TOPOLOGY: linear

    (ii) MOLECULE TYPE: protein

        (xi) SEQUENCE DESCRIPTION: SEQ ID NO:1:

Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
```

-continued

```
        115                 120                 125

    Leu Ala Asn Ser Met Leu Asn Ala Ser Gln Met Thr Gln Gly Asn Met
        130                 135                 140

    Asn Ala Phe Gly Ser Gly Val Asn Asn Ala Leu Ser Ser Ile Leu Gly
    145                 150                 155                 160

    Asn Gly Leu Gly Gln Ser Met Ser Gly Phe Ser Gln Pro Ser Leu Gly
                    165                 170                 175

    Ala Gly Gly Leu Gln Gly Leu Ser Gly Ala Gly Ala Phe Asn Gln Leu
                180                 185                 190

    Gly Asn Ala Ile Gly Met Gly Val Gly Gln Asn Ala Ala Leu Ser Ala
            195                 200                 205

    Leu Ser Asn Val Ser Thr His Val Asp Gly Asn Asn Arg His Phe Val
        210                 215                 220

    Asp Lys Glu Asp Arg Gly Met Ala Lys Glu Ile Gly Gln Phe Met Asp
    225                 230                 235                 240

    Gln Tyr Pro Glu Ile Phe Gly Lys Pro Glu Tyr Gln Lys Asp Gly Trp
                    245                 250                 255

    Ser Ser Pro Lys Thr Asp Asp Lys Ser Trp Ala Lys Ala Leu Ser Lys
                260                 265                 270

    Pro Asp Asp Asp Gly Met Thr Gly Ala Ser Met Asp Lys Phe Arg Gln
            275                 280                 285

    Ala Met Gly Met Ile Lys Ser Ala Val Ala Gly Asp Thr Gly Asn Thr
        290                 295                 300

    Asn Leu Asn Leu Arg Gly Ala Gly Gly Ala Ser Leu Gly Ile Asp Ala
    305                 310                 315                 320

    Ala Val Val Gly Asp Lys Ile Ala Asn Met Ser Leu Gly Lys Leu Ala
                    325                 330                 335

    Asn Ala
```

(2) INFORMATION FOR SEQ ID NO:2:

(i) SEQUENCE CHARACTERISTICS:
(A) LENGTH: 2141 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

```
CGATTTTACC CGGGTGAACG TGCTATGACC GACAGCATCA CGGTATTCGA CACCGTTACG     60

GCGTTTATGG CCGCGATGAA CCGGCATCAG GCGGCGCGCT GGTCGCCGCA ATCCGGCGTC    120

GATCTGGTAT TTCAGTTTGG GGACACCGGG CGTGAACTCA TGATGCAGAT TCAGCCGGGG    180

CAGCAATATC CCGGCATGTT GCGCACGCTG CTCGCTCGTC GTTATCAGCA GGCGGCAGAG    240

TGCGATGGCT GCCATCTGTG CCTGAACGGC AGCGATGTAT TGATCCTCTG GTGGCCGCTG    300

CCGTCGGATC CCGGCAGTTA TCCGCAGGTG ATCGAACGTT TGTTTGAACT GGCGGGAATG    360

ACGTTGCCGT CGCTATCCAT AGCACCGACG GCGCGTCCGC AGACAGGGAA CGGACGCGCC    420

CGATCATTAA GATAAAGGCG GCTTTTTTTA TTGCAAAACG GTAACGGTGA GGAACCGTTT    480

CACCGTCGGC GTCACTCAGT AACAAGTATC CATCATGATG CCTACATCGG GATCGGCGTG    540

GGCATCCGTT GCAGATACTT TTGCGAACAC CTGACATGAA TGAGGAAACG AAATTATGCA    600

AATTACGATC AAAGCGCACA TCGGCGGTGA TTTGGGCGTC TCCGGTCTGG GGCTGGGTGC    660

TCAGGGACTG AAAGGACTGA ATTCCGCGGC TTCATCGCTG GGTTCCAGCG TGGATAAACT    720
```

-continued

```
GAGCAGCACC ATCGATAAGT TGACCTCCGC GCTGACTTCG ATGATGTTTG GCGGCGCGCT    780

GGCGCAGGGG CTGGGCGCCA GCTCGAAGGG GCTGGGGATG AGCAATCAAC TGGGCCAGTC    840

TTTCGGCAAT GGCGCGCAGG GTGCGAGCAA CCTGCTATCC GTACCGAAAT CCGGCGGCGA    900

TGCGTTGTCA AAAATGTTTG ATAAAGCGCT GGACGATCTG CTGGGTCATG ACACCGTGAC    960

CAAGCTGACT AACCAGAGCA ACCAACTGGC TAATTCAATG CTGAACGCCA GCCAGATGAC   1020

CCAGGGTAAT ATGAATGCGT TCGGCAGCGG TGTGAACAAC GCACTGTCGT CCATTCTCGG   1080

CAACGGTCTC GGCCAGTCGA TGAGTGGCTT CTCTCAGCCT TCTCTGGGGG CAGGCGGCTT   1140

GCAGGGCCTG AGCGGCGCGG GTGCATTCAA CCAGTTGGGT AATGCCATCG GCATGGGCGT   1200

GGGGCAGAAT GCTGCGCTGA GTGCGTTGAG TAACGTCAGC ACCCACGTAG ACGGTAACAA   1260

CCGCCACTTT GTAGATAAAG AAGATCGCGG CATGGCGAAA GAGATCGGCC AGTTTATGGA   1320

TCAGTATCCG GAAATATTCG GTAAACCGGA ATACCAGAAA GATGGCTGGA GTTCGCCGAA   1380

GACGGACGAC AAATCCTGGG CTAAAGCGCT GAGTAAACCG GATGATGACG GTATGACCGG   1440

CGCCAGCATG GACAAATTCC GTCAGGCGAT GGGTATGATC AAAAGCGCGG TGGCGGGTGA   1500

TACCGGCAAT ACCAACCTGA ACCTGCGTGG CGCGGGCGGT GCATCGCTGG GTATCGATGC   1560

GGCTGTCGTC GGCGATAAAA TAGCCAACAT GTCGCTGGGT AAGCTGGCCA ACGCCTGATA   1620

ATCTGTGCTG GCCTGATAAA GCGGAAACGA AAAAAGAGAC GGGGAAGCCT GTCTCTTTTC   1680

TTATTATGCG GTTTATGCGG TTACCTGGAC CGGTTAATCA TCGTCATCGA TCTGGTACAA   1740

ACGCACATTT TCCCGTTCAT TCGCGTCGTT ACGCGCCACA ATCGCGATGG CATCTTCCTC   1800

GTCGCTCAGA TTGCGCGGCT GATGGGGAAC GCCGGGTGGA ATATAGAGAA ACTCGCCGGC   1860

CAGATGGAGA CACGTCTGCG ATAAATCTGT GCCGTAACGT GTTTCTATCC GCCCCTTTAG   1920

CAGATAGATT GCGGTTTCGT AATCAACATG GTAATGCGGT TCCGCCTGTG CGCCGGCCGG   1980

GATCACCACA ATATTCATAG AAAGCTGTCT TGCACCTACC GTATCGCGGG AGATACCGAC   2040

AAAATAGGGC AGTTTTTGCG TGGTATCCGT GGGGTGTTCC GGCCTGACAA TCTTGAGTTG   2100

GTTCGTCATC ATCTTTCTCC ATCTGGGCGA CCTGATCGGT T                       2141
```

(2) INFORMATION FOR SEQ ID NO:3:

(i) SEQUENCE CHARACTERISTICS:
(A) LENGTH: 403 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:3:

```
Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
        35                  40                  45

Gln Asn Asp Thr Val Asn Gln Leu Ala Gly Leu Leu Thr Gly Met Met
    50                  55                  60

Met Met Met Ser Met Met Gly Gly Gly Gly Leu Met Gly Gly Gly Leu
65                  70                  75                  80

Gly Gly Gly Leu Gly Asn Gly Leu Gly Gly Ser Gly Gly Leu Gly Glu
                85                  90                  95

Gly Leu Ser Asn Ala Leu Asn Asp Met Leu Gly Gly Ser Leu Asn Thr
```

-continued

```
                100                 105                 110

Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala
```

(2) INFORMATION FOR SEQ ID NO:4:

(i) SEQUENCE CHARACTERISTICS:
(A) LENGTH: 1288 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

```
AAGCTTCGGC ATGGCACGTT TGACCGTTGG GTCGGCAGGG TACGTTTGAA TTATTCATAA     60

GAGGAATACG TTATGAGTCT GAATACAAGT GGGCTGGGAG CGTCAACGAT GCAAATTTCT    120

ATCGGCGGTG CGGGCGGAAA TAACGGGTTG CTGGGTACCA GTCGCCAGAA TGCTGGGTTG    180

GGTGGCAATT CTGCACTGGG GCTGGGCGGC GGTAATCAAA ATGATACCGT CAATCAGCTG    240

GCTGGCTTAC TCACCGGCAT GATGATGATG ATGAGCATGA TGGGCGGTGG TGGGCTGATG    300
```

-continued

```
GGCGGTGGCT TAGGCGGTGG CTTAGGTAAT GGCTTGGGTG GCTCAGGTGG CCTGGGCGAA    360
GGACTGTCGA ACGCGCTGAA CGATATGTTA GGCGGTTCGC TGAACACGCT GGGCTCGAAA    420
GGCGGCAACA ATACCACTTC AACAACAAAT TCCCCGCTGG ACCAGGCGCT GGGTATTAAC    480
TCAACGTCCC AAAACGACGA TTCCACCTCC GGCACAGATT CCACCTCAGA CTCCAGCGAC    540
CCGATGCAGC AGCTGCTGAA GATGTTCAGC GAGATAATGC AAAGCCTGTT TGGTGATGGG    600
CAAGATGGCA CCCAGGGCAG TTCCTCTGGG GGCAAGCAGC CGACCGAAGG CGAGCAGAAC    660
GCCTATAAAA AAGGAGTCAC TGATGCGCTG TCGGGCCTGA TGGGTAATGG TCTGAGCCAG    720
CTCCTTGGCA ACGGGGGACT GGGAGGTGGT CAGGGCGGTA ATGCTGGCAC GGGTCTTGAC    780
GGTTCGTCGC TGGGCGGCAA AGGGCTGCAA AACCTGAGCG GGCCGGTGGA CTACCAGCAG    840
TTAGGTAACG CCGTGGGTAC CGGTATCGGT ATGAAAGCGG GCATTCAGGC GCTGAATGAT    900
ATCGGTACGC ACAGGCACAG TTCAACCCGT TCTTTCGTCA ATAAAGGCGA TCGGGCGATG    960
GCGAAGGAAA TCGGTCAGTT CATGGACCAG TATCCTGAGG TGTTTGGCAA GCCGCAGTAC   1020
CAGAAAGGCC CGGGTCAGGA GGTGAAAACC GATGACAAAT CATGGGCAAA AGCACTGAGC   1080
AAGCCAGATG ACGACGGAAT GACACCAGCC AGTATGGAGC AGTTCAACAA AGCCAAGGGC   1140
ATGATCAAAA GGCCCATGGC GGGTGATACC GGCAACGGCA ACCTGCAGGC ACGCGGTGCC   1200
GGTGGTTCTT CGCTGGGTAT TGATGCCATG ATGGCCGGTG ATGCCATTAA CAATATGGCA   1260
CTTGGCAAGC TGGGCGCGGC TTAAGCTT                                      1288
```

(2) INFORMATION FOR SEQ ID NO:5:

(i) SEQUENCE CHARACTERISTICS:
(A) LENGTH: 341 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:5:

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25                  30

Ser Lys Ala Leu Gln Glu Val Val Val Lys Leu Ala Glu Glu Leu Met
        35                  40                  45

Arg Asn Gly Gln Leu Asp Asp Ser Ser Pro Leu Gly Lys Leu Leu Ala
    50                  55                  60

Lys Ser Met Ala Ala Asp Gly Lys Ala Gly Gly Gly Ile Glu Asp Val
65                  70                  75                  80

Ile Ala Ala Leu Asp Lys Leu Ile His Glu Lys Leu Gly Asp Asn Phe
                85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175
```

```
Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Gly Leu Leu Leu Lys Gly Leu Glu Ala
    290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
            340
```

(2) INFORMATION FOR SEQ ID NO:6:

(i) SEQUENCE CHARACTERISTICS:
(A) LENGTH: 1026 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

```
ATGCAGAGTC TCAGTCTTAA CAGCAGCTCG CTGCAAACCC CGGCAATGGC CCTTGTCCTG     60

GTACGTCCTG AAGCCGAGAC GACTGGCAGT ACGTCGAGCA AGGCGCTTCA GGAAGTTGTC    120

GTGAAGCTGG CCGAGGAACT GATGCGCAAT GGTCAACTCG ACGACAGCTC GCCATTGGGA    180

AAACTGTTGG CCAAGTCGAT GGCCGCAGAT GGCAAGGCGG GCGGCGGTAT TGAGGATGTC    240

ATCGCTGCGC TGGACAAGCT GATCCATGAA AAGCTCGGTG ACAACTTCGG CGCGTCTGCG    300

GACAGCGCCT CGGGTACCGG ACAGCAGGAC CTGATGACTC AGGTGCTCAA TGGCCTGGCC    360

AAGTCGATGC TCGATGATCT TCTGACCAAG CAGGATGGCG GGACAAGCTT CTCCGAAGAC    420

GATATGCCGA TGCTGAACAA GATCGCGCAG TTCATGGATG ACAATCCCGC ACAGTTTCCC    480

AAGCCGGACT CGGGCTCCTG GGTGAACGAA CTCAAGGAAG ACAACTTCCT TGATGGCGAC    540

GAAACGGCTG CGTTCCGTTC GGCACTCGAC ATCATTGGCC AGCAACTGGG TAATCAGCAG    600

AGTGACGCTG GCAGTCTGGC AGGGACGGGT GGAGGTCTGG GCACTCCGAG CAGTTTTTCC    660

AACAACTCGT CCGTGATGGG TGATCCGCTG ATCGACGCCA ATACCGGTCC CGGTGACAGC    720

GGCAATACCC GTGGTGAAGC GGGGCAACTG ATCGGCGAGC TTATCGACCG TGGCCTGCAA    780

TCGGTATTGG CCGGTGGTGG ACTGGGCACA CCCGTAAACA CCCCGCAGAC CGGTACGTCG    840

GCGAATGGCG GACAGTCCGC TCAGGATCTT GATCAGTTGC TGGGCGGCTT GCTGCTCAAG    900

GGCCTGGAGG CAACGCTCAA GGATGCCGGG CAAACAGGCA CCGACGTGCA GTCGAGCGCT    960

GCGCAAATCG CCACCTTGCT GGTCAGTACG CTGCTGCAAG GCACCCGCAA TCAGGCTGCA   1020
```

GCCTGA 1026

(2) INFORMATION FOR SEQ ID NO:7:

(i) SEQUENCE CHARACTERISTICS:
(A) LENGTH: 344 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:7:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
```

340

(2) INFORMATION FOR SEQ ID NO:8:

(i) SEQUENCE CHARACTERISTICS:
(A) LENGTH: 1035 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

```
ATGTCAGTCG GAAACATCCA GAGCCCGTCG AACCTCCCGG GTCTGCAGAA CCTGAACCTC     60

AACACCAACA CCAACAGCCA GCAATCGGGC CAGTCCGTGC AAGACCTGAT CAAGCAGGTC    120

GAGAAGGACA TCCTCAACAT CATCGCAGCC CTCGTGCAGA AGGCCGCACA GTCGGCGGGC    180

GGCAACACCG GTAACACCGG CAACGCGCCG GCGAAGGACG GCAATGCCAA CGCGGGCGCC    240

AACGACCCGA GCAAGAACGA CCCGAGCAAG AGCCAGGCTC CGCAGTCGGC CAACAAGACC    300

GGCAACGTCG ACGACGCCAA CAACCAGGAT CCGATGCAAG CGCTGATGCA GCTGCTGGAA    360

GACCTGGTGA AGCTGCTGAA GGCGGCCCTG CACATGCAGC AGCCCGGCGG CAATGACAAG    420

GGCAACGGCG TGGGCGGTGC CAACGGCGCC AAGGGTGCCG GCGGCCAGGG CGGCCTGGCC    480

GAAGCGCTGC AGGAGATCGA GCAGATCCTC GCCCAGCTCG GCGGCGGCGG TGCTGGCGCC    540

GGCGGCGCGG GTGGCGGTGT CGGCGGTGCT GGTGGCGCGG ATGGCGGCTC CGGTGCGGGT    600

GGCGCAGGCG GTGCGAACGG CGCCGACGGC GGCAATGGCG TGAACGGCAA CCAGGCGAAC    660

GGCCCGCAGA ACGCAGGCGA TGTCAACGGT GCCAACGGCG CGGATGACGG CAGCGAAGAC    720

CAGGGCGGCC TCACCGGCGT GCTGCAAAAG CTGATGAAGA TCCTGAACGC GCTGGTGCAG    780

ATGATGCAGC AAGGCGGCCT CGGCGGCGGC AACCAGGCGC AGGGCGGCTC GAAGGGTGCC    840

GGCAACGCCT CGCCGGCTTC CGGCGCGAAC CCGGGCGCGA ACCAGCCCGG TTCGGCGGAT    900

GATCAATCGT CCGGCCAGAA CAATCTGCAA TCCCAGATCA TGGATGTGGT GAAGGAGGTC    960

GTCCAGATCC TGCAGCAGAT GCTGGCGGCG CAGAACGGCG GCAGCCAGCA GTCCACCTCG   1020

ACGCAGCCGA TGTAA                                                    1035
```

(2) INFORMATION FOR SEQ ID NO:9:

(i) SEQUENCE CHARACTERISTICS:
(A) LENGTH: 26 amino acids
(B) TYPE: amino acid
(C) STRANDEDNESS:
(D) TOPOLOGY: linear (ii) MOLECULE TYPE: protein (xi) SEQUENCE DESCRIPTION: SEQ ID NO:9:

```
Thr Leu Ile Glu Leu Met Ile Val Val Ala Ile Ile Ala Ile Leu Ala
1               5                   10                  15

Ala Ile Ala Leu Pro Ala Tyr Gln Asp Tyr
            20                  25
```

(2) INFORMATION FOR SEQ ID NO:10:

(i) SEQUENCE CHARACTERISTICS:
(A) LENGTH: 20 amino acids
(B) TYPE: amino acid
(C) STRANDEDNESS:
(D) TOPOLOGY: linear (ii) MOLECULE TYPE: protein -continued

```
     (xi) SEQUENCE DESCRIPTION: SEQ ID NO:10:

   Ser Ser Gln Gln Ser Pro Ser Ala Gly Ser Glu Gln Gln Leu Asp Gln
   1               5                  10                  15

   Leu Leu Ala Met
               20
```

INSECT CONTROL WITH A HYPERSENSITIVE RESPONSE ELICITOR

This application claims the benefit of U.S. Provisional patent application Ser. No. 60/039,226, filed Feb. 28, 1997.

FIELD OF THE INVENTION

The present invention relates to the control of insects.

BACKGROUND OF THE INVENTION

The introduction of synthetic organic pesticides following World War II brought inestimable benefits to humanity and agricultural economic profitability. The widescale deployment of DDT resulted in the complete riddance, from entire countries, of serious public pests such as malaria mosquitoes. The use of DDT, other organochlorines, and, later, organophosphorus and carbamate materials was enthusiastically adopted into control programs despite occasional warnings about the hazard of unilateral approaches to pest control.

The development of new pesticides and the increasing amounts of pesticides used for pest control are closely correlated with the development of pest resistance to chemicals. The number of pesticide resistant species has greatly increased since the adoption of DDT in 1948. As a result, by the 1980s, the number of reports of pesticide resistance for arthropod pests was listed as 281, for plant pathogens 67, and for weeds 17. These numbers have steadily increased to the present day. Thus, the need for biological control agents, especially those with broadbase activity is especially important.

The present invention is directed to overcoming these problems in the art.

SUMMARY OF THE INVENTION

The present invention relates to a method of insect control for plants. This method involves applying a hypersensitive response elicitor polypeptide or protein in a non-infectious form to plants or plant seeds under conditions effective to control insects on the plants or plants grown from the plant seeds.

As an alternative to applying a hypersensitive response elicitor polypeptide or protein to plants or plant seeds in order to control insects on plants or plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to control insects. Alternatively, a transgenic plant seed transformed with a DNA molecule encoding a hypersensitive response elicitor polypeptide or protein can be provided and planted in soil. A plant is then propagated from the planted seed under conditions effective to control insects.

The present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection.

As a result, the present invention provides significant economic benefit to growers.

BRIEF DESCRIPTION OF THE DRAWINGS

FIG. 1 is a plot for the field study of Example 4.

DETAILED DESCRIPTION OF THE INVENTION

Figure 2:
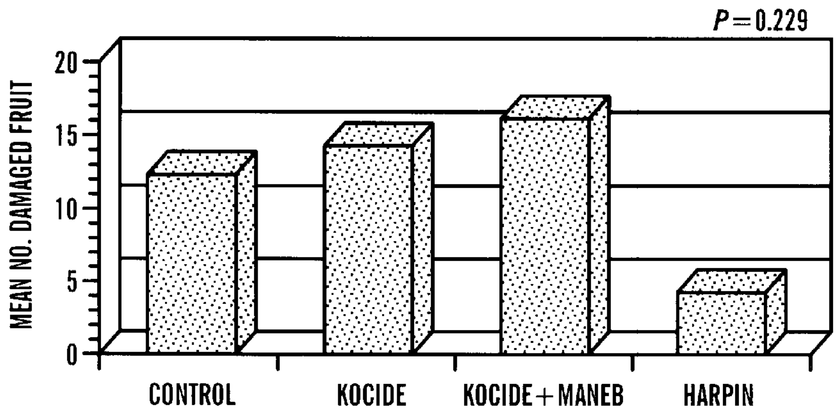
FIG. 2 shows the mean number of pepper fruit lost to bacterial soft rot for control, Kocide, Kocide+Maneb, and hypersensitive response elicitor ("harpin") treatments predisposed by European Corn Borer.

The present invention relates to a method of insect control for plants. This method involves applying a hypersensitive response elicitor polypeptide or protein in a non-infectious form to all or part of a plant or a plant seed under conditions to control insects on plants or plants grown from the plant seed. Alternatively, the hypersensitive response elicitor protein or polypeptide can be applied to plants such that seeds recovered from such plants are themselves effective to control insects.

As an alternative to applying a hypersensitive response elicitor polypeptide or protein to plants or plant seeds in order to control insects on the plants or plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to control insects. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to control insects.

The hypersensitive response elicitor polypeptide or protein utilized in the present invention can correspond to hypersensitive response elicitor polypeptides or proteins derived from a wide variety of fungal and bacterial pathogens. Such polypeptides or proteins are able to elicit local necrosis in plant tissue contacted by the elicitor. Examples of suitable bacterial sources of polypeptide or protein elicitors include Erwinia, Pseudomonas, and Xanthamonas species (e.g., the following bacteria: *Erwinia amylovora, Erwinia chrysanthemi, Erwinia stewartii, Erwinia carotovora, Pseudomonas syringae, Pseudomonas solancearum, Xanthomonas campestris,* and mixtures thereof).

An example of a fungal source of a hypersensitive response elicitor protein or polypeptide is Phytophthora. Suitable species of Phytophthora include *Phytophthora pythium, Phytophthora cryptogea, Phytophthora cinnamomi, Phytophthora capsici, Phytophthora megasperma,* and *Phytophthora citrophthora.*

The embodiment of the present invention where the hypersensitive response elicitor polypeptide or protein is applied to the plant or plant seed can be carried out in a number of ways, including: 1) application of an isolated elicitor polypeptide or protein; 2) application of bacteria which do not cause disease and are transformed with genes encoding a hypersensitive response elicitor polypeptide or protein; and 3) application of bacteria which cause disease in some plant species (but not in those to which they are applied) and naturally contain a gene encoding the hypersensitive response elicitor polypeptide or protein. In addition, seeds in accordance with the present invention can be recovered from plants which have been treated with a hypersensitive response elicitor protein or polypeptide in accordance with the present invention.

In one embodiment of the present invention, the hypersensitive response elicitor polypeptides or proteins can be isolated from their corresponding organisms and applied to plants or plant seeds. Such isolation procedures are well known, as described in Arlat, M., F. Van Gijsegem, J. C. Huet, J. C. Pemollet, and C. A. Boucher, "PopA1, a Protein which Induces a Hypersensitive-like Response in Specific Petunia Genotypes is Secreted via the Hrp Pathway of *Pseudomonas solanacearum," EMBO J.* 13:543–553 (1994); He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993); and Wei, Z.-M., R. J. Laby, C. H. Zumoff, D. W. Bauer, S.-Y. He, A. Collmer, and S. V. Beer, "Harpin Elicitor of the Hypersensitive Response Produced by the Plant Pathogen *Erwinia amylovora", Science* 257:85–88 (1992), which are hereby incorporated by reference. See also pending U.S. patent application Ser. Nos. 08/200,024 and 08/062,024, which are hereby incorporated by reference. Preferably, however, the isolated hypersensitive response elicitor polypeptides or proteins of the present invention are produced recombinantly and purified as described below.

In other embodiments of the present invention, the hypersensitive response elicitor polypeptide or protein of the present invention can be applied to plants or plant seeds by applying bacteria containing genes encoding the hypersensitive response elicitor polypeptide or protein. Such bacteria must be capable of secreting or exporting the polypeptide or protein so that the elicitor can contact plant or plant seeds cells. In these embodiments, the hypersensitive response elicitor polypeptide or protein is produced by the bacteria in planta or on seeds or just prior to introduction of the bacteria to the plants or plant seeds.

In one embodiment of the bacterial application mode of the present invention, the bacteria do not cause the disease and have been transformed (e.g., recombinantly) with genes encoding a hypersensitive response elicitor polypeptide or protein. For example, *E. coli,* which does not elicit a hypersensitive response in plants, can be transformed with genes encoding a hypersensitive response elicitor polypeptide or protein and then applied to plants. Bacterial species other than *E. coli* can also be used in this embodiment of the present invention.

In another embodiment of the bacterial application mode of the present invention, the bacteria do cause disease and naturally contain a gene encoding a hypersensitive response elicitor polypeptide or protein. Examples of such bacteria are noted above. However, in this embodiment, these bacteria are applied to plants or their seeds which are not susceptible to the disease carried by the bacteria. For example, *Erwinia amylovora* causes disease in apple or pear but not in tomato. However, such bacteria will elicit a hypersensitive response in tomato. Accordingly, in accordance with this embodiment of the present invention, *Erwinia amylovora* can be applied to tomato plants or seeds to enhance growth without causing disease in that species.

The hypersensitive response elicitor polypeptide or protein from *Erwinia chrysanthemi* has an amino acid sequence corresponding to SEQ. ID. No. 1 as follows:

| | | | | | | | | | | | | | | | |
|---|---|---|---|---|---|---|---|---|---|---|---|---|---|---|---|
| Met | Gln | Ile | Thr | Ile | Lys | Ala | His | Ile | Gly | Gly | Asp | Leu | Gly | Val | Ser |
| 1 | | | | 5 | | | | | 10 | | | | | 15 | |
| Gly | Leu | Gly | Ala | Gln | Gly | Leu | Lys | Gly | Leu | Asn | Ser | Ala | Ala | Ser | Ser |
| | | | 20 | | | | | 25 | | | | | 30 | | |
| Leu | Gly | Ser | Ser | Val | Asp | Lys | Leu | Ser | Ser | Thr | Ile | Asp | Lys | Leu | Thr |
| | | 35 | | | | | 40 | | | | | 45 | | | |
| Ser | Ala | Leu | Thr | Ser | Met | Met | Phe | Gly | Gly | Ala | Leu | Ala | Gln | Gly | Leu |
| | 50 | | | | | 55 | | | | | 60 | | | | |
| Gly | Ala | Ser | Ser | Lys | Gly | Leu | Gly | Met | Ser | Asn | Gln | Leu | Gly | Gln | Ser |
| 65 | | | | | 70 | | | | | 75 | | | | | 80 |
| Phe | Gly | Asn | Gly | Ala | Gln | Gly | Ala | Ser | Asn | Leu | Leu | Ser | Val | Pro | Lys |
| | | | | 85 | | | | | 90 | | | | | 95 | |
| Ser | Gly | Gly | Asp | Ala | Leu | Ser | Lys | Met | Phe | Asp | Lys | Ala | Leu | Asp | Asp |
| | | | 100 | | | | | 105 | | | | | 110 | | |
| Leu | Leu | Gly | His | Asp | Thr | Val | Thr | Lys | Leu | Thr | Asn | Gln | Ser | Asn | Gln |
| | | 115 | | | | | 120 | | | | | 125 | | | |
| Leu | Ala | Asn | Ser | Met | Leu | Asn | Ala | Ser | Gln | Met | Thr | Gln | Gly | Asn | Met |
| | 130 | | | | | 135 | | | | | 140 | | | | |
| Asn | Ala | Phe | Gly | Ser | Gly | Val | Asn | Asn | Ala | Leu | Ser | Ser | Ile | Leu | Gly |
| 145 | | | | | 150 | | | | | 155 | | | | | 160 |
| Asn | Gly | Leu | Gly | Gln | Ser | Met | Ser | Gly | Phe | Ser | Gln | Pro | Ser | Leu | Gly |
| | | | | 165 | | | | | 170 | | | | | 175 | |

-continued

```
Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

This hypersensitive response elicitor polypeptide or protein has a molecular weight of 34 kDa, is heat stable, has a glycine content of greater than 16%, and contains substantially no cysteine. The *Erwinia chrysanthemi* hypersensitive response elicitor polypeptide or protein is encoded by a DNA molecule having a nucleotide sequence corresponding to SEQ. ID. No. 2 as follows:

```
CGATTTTACC CGGGTGAACG TGCTATGACC GACAGCATCA CGGTATTCGA CACCGTTACG   60

GCGTTTATGG CCGCGATGAA CCGGCATCAG GCGGCGCGCT GGTCGCCGCA ATCCGGCGTC  120

GATCTGGTAT TTCAGTTTGG GGACACCGGG CGTGAACTCA TGATGCAGAT TCAGCCGGGG  180

CAGCAATATC CCGGCATGTT GCGCACGCTG CTCGCTCGTC GTTATCAGCA GGCGGCAGAG  240

TGCGATGGCT GCCATCTGTG CCTGAACGGC AGCGATGTAT TGATCCTCTG GTGGCCGCTG  300

CCGTCGGATC CCGGCAGTTA TCCGCAGGTG ATCGAACGTT TGTTTGAACT GGCGGGAATG  360

ACGTTGCCGT CGCTATCCAT AGCACCGACG GCGCGTCCGC AGACAGGGAA CGGACGCGCC  420

CGATCATTAA GATAAAGGCG GCTTTTTTTA TTGCAAAACG GTAACGGTGA GGAACCGTTT  480

CACCGTCGGC GTCACTCAGT AACAAGTATC CATCATGATG CCTACATCGG GATCGGCGTG  540

GGCATCCGTT GCAGATACTT TTGCGAACAC CTGACATGAA TGAGGAAACG AAATTATGCA  600

AATTACGATC AAAGCGCACA TCGGCGGTGA TTTGGGCGTC TCCGGTCTGG GCTGGGTGC   660

TCAGGGACTG AAAGGACTGA ATTCCGCGGC TTCATCGCTG GGTTCCAGCG TGGATAAACT  720

GAGCAGCACC ATCGATAAGT TGACCTCCGC GCTGACTTCG ATGATGTTTG GCGGCGCGCT  780

GGCGCAGGGG CTGGGCGCCA GCTCGAAGGG GCTGGGGATG AGCAATCAAC TGGGCCAGTC  840

TTTCGGCAAT GGCGCGCAGG GTGCGAGCAA CCTGCTATCC GTACCGAAAT CCGGCGGCGA  900

TGCGTTGTCA AAAATGTTTG ATAAAGCGCT GGACGATCTG CTGGGTCATG ACACCGTGAC  960

CAAGCTGACT AACCAGAGCA ACCAACTGGC TAATTCAATG CTGAACGCCA GCCAGATGAC 1020

CCAGGGTAAT ATGAATGCGT TCGGCAGCGG TGTGAACAAC GCACTGTCGT CCATTCTCGG 1080

CAACGGTCTC GGCCAGTCGA TGAGTGGCTT CTCTCAGCCT TCTCTGGGGG CAGGCGGCTT 1140
```

-continued

| | | | | | | |
|---|---|---|---|---|---|---|
| GCAGGGCCTG | AGCGGCGCGG | GTGCATTCAA | CCAGTTGGGT | AATGCCATCG | GCATGGGCGT | 1200 |
| GGGGCAGAAT | GCTGCGCTGA | GTGCGTTGAG | TAACGTCAGC | ACCCACGTAG | ACGGTAACAA | 1260 |
| CCGCCACTTT | GTAGATAAAG | AAGATCGCGG | CATGGCGAAA | GAGATCGGCC | AGTTTATGGA | 1320 |
| TCAGTATCCG | GAAATATTCG | GTAAACCGGA | ATACCAGAAA | GATGGCTGGA | GTTCGCCGAA | 1380 |
| GACGGACGAC | AAATCCTGGG | CTAAAGCGCT | GAGTAAACCG | GATGATGACG | GTATGACCGG | 1440 |
| CGCCAGCATG | GACAAATTCC | GTCAGGCGAT | GGGTATGATC | AAAAGCGCGG | TGGCGGGTGA | 1500 |
| TACCGGCAAT | ACCAACCTGA | ACCTGCGTGG | CGCGGGCGGT | GCATCGCTGG | GTATCGATGC | 1560 |
| GGCTGTCGTC | GGCGATAAAA | TAGCCAACAT | GTCGCTGGGT | AAGCTGGCCA | ACGCCTGATA | 1620 |
| ATCTGTGCTG | GCCTGATAAA | GCGGAAACGA | AAAAAGAGAC | GGGGAAGCCT | GTCTCTTTTC | 1680 |
| TTATTATGCG | GTTTATGCGG | TTACCTGGAC | CGGTTAATCA | TCGTCATCGA | TCTGGTACAA | 1740 |
| ACGCACATTT | TCCCGTTCAT | TCGCGTCGTT | ACGCGCCACA | ATCGCGATGG | CATCTTCCTC | 1800 |
| GTCGCTCAGA | TTGCGCGGCT | GATGGGGAAC | GCCGGGTGGA | ATATAGAGAA | ACTCGCCGGC | 1860 |
| CAGATGGAGA | CACGTCTGCG | ATAAATCTGT | GCCGTAACGT | GTTTCTATCC | GCCCCTTTAG | 1920 |
| CAGATAGATT | GCGGTTTCGT | AATCAACATG | GTAATGCGGT | TCCGCCTGTG | CGCCGGCCGG | 1980 |
| GATCACCACA | ATATTCATAG | AAAGCTGTCT | TGCACCTACC | GTATCGCGGG | AGATACCGAC | 2040 |
| AAAATAGGGC | AGTTTTTGCG | TGGTATCCGT | GGGGTGTTCC | GGCCTGACAA | TCTTGAGTTG | 2100 |
| GTTCGTCATC | ATCTTTCTCC | ATCTGGGCGA | CCTGATCGGT | T | | 2141 |

The hypersensitive response elicitor polypeptide or protein derived from *Erwinia amylovora* has an amino acid sequence corresponding to SEQ. ID. No. 3 as follows:

```
Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
        35                  40                  45

Gln Asn Asp Thr Val Asn Gln Leu Ala Gly Leu Leu Thr Gly Met Met
    50                  55                  60

Met Met Met Ser Met Met Gly Gly Gly Gly Leu Met Gly Gly Gly Leu
65                  70                  75                  80

Gly Gly Gly Leu Gly Asn Gly Leu Gly Gly Ser Gly Gly Leu Gly Glu
                85                  90                  95

Gly Leu Ser Asn Ala Leu Asn Asp Met Leu Gly Gly Ser Leu Asn Thr
            100                 105                 110

Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190
```

-continued

```
Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala
```

This hypersensitive response elicitor polypeptide or protein has a molecular weight of about 39 kDa, has a pI of approximately 4.3, and is heat stable at 100° C. for at least 10 minutes. This hypersensitive response elicitor polypeptide or protein has substantially no cysteine. The hypersensitive response elicitor polypeptide or protein derived from *Erwinia amylovora* is more fully described in Wei, Z.-M., R. J. Laby, C. H. Zumoff, D. W. Bauer, S.-Y. He, A. Collmer, and S. V. Beer, "Harpin, Elicitor of the Hypersensitive Response Produced by the Plant Pathogen *Erwinia amylovora*," *Science* 257:85–88 (1992), which is hereby incorporated by reference. The DNA molecule encoding this polypeptide or protein has a nucleotide sequence corresponding to SEQ. ID. No. 4 as follows:

```
AAGCTTCGGC ATGGCACGTT TGACCGTTGG GTCGGCAGGG TACGTTTGAA TTATTCATAA    60

GAGGAATACG TTATGAGTCT GAATACAAGT GGGCTGGGAG CGTCAACGAT GCAAATTTCT   120

ATCGGCGGTG CGGGCGGAAA TAACGGGTTG CTGGGTACCA GTCGCCAGAA TGCTGGGTTG   180

GGTGGCAATT CTGCACTGGG GCTGGGCGGC GGTAATCAAA ATGATACCGT CAATCAGCTG   240

GCTGGCTTAC TCACCGGCAT GATGATGATG ATGAGCATGA TGGGCGGTGG TGGGCTGATG   300

GGCGGTGGCT TAGGCGGTGG CTTAGGTAAT GGCTTGGGTG GCTCAGGTGG CCTGGGCGAA   360

GGACTGTCGA ACGCGCTGAA CGATATGTTA GGCGGTTCGC TGAACACGCT GGGCTCGAAA   420

GGCGGCAACA ATACCACTTC AACAACAAAT TCCCCGCTGG ACCAGGCGCT GGGTATTAAC   480

TCAACGTCCC AAAACGACGA TTCCACCTCC GGCACAGATT CCACCTCAGA CTCCAGCGAC   540

CCGATGCAGC AGCTGCTGAA GATGTTCAGC GAGATAATGC AAAGCCTGTT TGGTGATGGG   600

CAAGATGGCA CCCAGGGCAG TTCCTCTGGG GGCAAGCAGC CGACCGAAGG CGAGCAGAAC   660

GCCTATAAAA AAGGAGTCAC TGATGCGCTG TCGGGCCTGA TGGGTAATGG TCTGAGCCAG   720

CTCCTTGGCA ACGGGGGACT GGGAGGTGGT CAGGGCGGTA ATGCTGGCAC GGGTCTTGAC   780
```

-continued

| | | | | | | |
|---|---|---|---|---|---|---|
| GGTTCGTCGC | TGGGCGGCAA | AGGGCTGCAA | AACCTGAGCG | GGCCGGTGGA | CTACCAGCAG | 840 |
| TTAGGTAACG | CCGTGGGTAC | CGGTATCGGT | ATGAAAGCGG | GCATTCAGGC | GCTGAATGAT | 900 |
| ATCGGTACGC | ACAGGCACAG | TTCAACCCGT | TCTTTCGTCA | ATAAAGGCGA | TCGGGCGATG | 960 |
| GCGAAGGAAA | TCGGTCAGTT | CATGGACCAG | TATCCTGAGG | TGTTTGGCAA | GCCGCAGTAC | 1020 |
| CAGAAAGGCC | CGGGTCAGGA | GGTGAAAACC | GATGACAAAT | CATGGGCAAA | AGCACTGAGC | 1080 |
| AAGCCAGATG | ACGACGGAAT | GACACCAGCC | AGTATGGAGC | AGTTCAACAA | AGCCAAGGGC | 1140 |
| ATGATCAAAA | GGCCCATGGC | GGGTGATACC | GGCAACGGCA | ACCTGCAGGC | ACGCGGTGCC | 1200 |
| GGTGGTTCTT | CGCTGGGTAT | TGATGCCATG | ATGGCCGGTG | ATGCCATTAA | CAATATGGCA | 1260 |
| CTTGGCAAGC | TGGGCGCGGC | TTAAGCTT | | | | 1288 |

The hypersensitive response elicitor polypeptide or protein derived from *Pseudomonas syringae* has an amino acid sequence corresponding to SEQ. ID. No. 5 as follows:

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25                  30

Ser Lys Ala Leu Gln Glu Val Val Val Lye Seu Ala Glu Glu Leu Met
        35                  40                  45

Arg Asn Gly Gln Leu Asp Asp Ser Ser Pro Leu Gly Lys Leu Leu Ala
    50                  55                  60

Lys Ser Met Ala Ala Asp Gly Lys Ala Gly Gly Gly Ile Glu Asp Val
65                  70                  75                  80

Ile Ala Ala Leu Asp Lys Leu Ile His Glu Lys Leu Gly Asp Asn Phe
                85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285
```

-continued

| | | | | | | | | | | | | | | | |
|---|---|---|---|---|---|---|---|---|---|---|---|---|---|---|---|
| Asp | Leu | Asp | Gln | Leu | Leu | Gly | Gly | Leu | Leu | Leu | Lys | Gly | Leu | Glu | Ala |
| | 290 | | | | | 295 | | | | | 300 | | | | |
| Thr | Leu | Lys | Asp | Ala | Gly | Gln | Thr | Gly | Thr | Asp | Val | Gln | Ser | Ser | Ala |
| 305 | | | | | 310 | | | | | 315 | | | | | 320 |
| Ala | Gln | Ile | Ala | Thr | Leu | Leu | Val | Ser | Thr | Leu | Leu | Gln | Gly | Thr | Arg |
| | | | | 325 | | | | | 330 | | | | | 335 | |
| Asn | Gln | Ala | Ala | Ala | | | | | | | | | | | |
| | | | 340 | | | | | | | | | | | | |

This hypersensitive response elicitor polypeptide or protein has a molecular weight of 34–35 kDa. It is rich in glycine (about 13.5%) and lacks cysteine and tyrosine. Further information about the hypersensitive response elicitor derived from *Pseudomonas syringae* is found in He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993), which is hereby incorporated by reference. The DNA molecule encoding the hypersensitive response elicitor from *Pseudomonas syringae* has a nucleotide sequence corresponding to SEQ. ID. No. 6 as follows:

```
ATGCAGAGTC TCAGTCTTAA CAGCAGCTCG CTGCAAACCC CGGCAATGGC CCTTGTCCTG   60
GTACGTCCTG AAGCCGAGAC GACTGGCAGT ACGTCGAGCA AGGCGCTTCA GGAAGTTGTC  120
GTGGAAGCTGG CCGAGGACT GATGCGCAAT GGTCAACTCG ACGACAGCTC GCCATTGGGA  180
AAACTGTTGG CCAAGTCGAT GGCCGCAGAT GGCAAGGCGG GCGGCGGTAT TGAGGATGTC  240
ATCGCTGCGC TGGACAAGCT GATCCATGAA AAGCTCGGTG ACAACTTCGG CGCGTCTGCG  300
GACAGCGCCT CGGGTACCGG ACAGCAGGAC CTGATGACTC AGGTGCTCAA TGGCCTGGCC  360
AAGTCGATGC TCGATGATCT TCTGACCAAG CAGGATGGCG GGACAAGCTT CTCCGAAGAC  420
GATATGCCGA TGCTGAACAA GATCGCGCAG TTCATGGATG ACAATCCCGC ACAGTTTCCC  480
AAGCCGGACT CGGGCTCCTG GGTGAACGAA CTCAAGGAAG ACAACTTCCT TGATGGCGAC  540
GAAACGGCTG CGTTCCGTTC GGCACTCGAC ATCATTGGCC AGCAACTGGG TAATCAGCAG  600
AGTGACGCTG GCAGTCTGGC AGGGACGGGT GGAGGTCTGG GCACTCCGAG CAGTTTTTCC  660
AACAACTCGT CCGTGATGGG TGATCCGCTG ATCGACGCCA ATACCGGTCC CGGTGACAGC  720
GGCAATACCC GTGGTGAAGC GGGGCAACTG ATCGGCGAGC TTATCGACCG TGGCCTGCAA  780
TCGGTATTGG CCGGTGGTGG ACTGGGCACA CCCGTAAACA CCCCGCAGAC CGGTACGTCG  840
GCGAATGGCG GACAGTCCGC TCAGGATCTT GATCAGTTGC TGGGCGGCTT GCTGCTCAAG  900
GGCCTGGAGG CAACGCTCAA GGATGCCGGG CAAACAGGCA CCGACGTGCA GTCGAGCGCT  960
GCGCAAATCG CCACCTTGCT GGTCAGTACG CTGCTGCAAG GCACCCGCAA TCAGGCTGCA 1020
GCCTGA                                                           1026
```

The hypersensitive response elicitor polypeptide or protein derived from *Pseudomonas solanacearum* has an amino acid sequence corresponding to SEQ. ID. No. 7 as follows:

| | | | | | | | | | | | | | | | |
|---|---|---|---|---|---|---|---|---|---|---|---|---|---|---|---|
| Met | Ser | Val | Gly | Asn | Ile | Gln | Ser | Pro | Ser | Asn | Leu | Pro | Gly | Leu | Gln |
| 1 | | | | 5 | | | | | 10 | | | | | 15 | |
| Asn | Leu | Asn | Leu | Asn | Thr | Asn | Thr | Asn | Ser | Gln | Gln | Ser | Gly | Gln | Ser |
| | | | 20 | | | | | 25 | | | | | 30 | | |
| Val | Gln | Asp | Leu | Ile | Lys | Gln | Val | Glu | Lys | Asp | Ile | Leu | Asn | Ile | Ile |
| | | 35 | | | | | 40 | | | | | 45 | | | |

-continued

Ala Ala Leu Val Gln Lys Ala Ala Gln Ser Ala Gly Gly Asn Thr Gly
50 55 60

Asn Thr Gly Asn Ala Pro Ala Lys Asp Gly Asn Ala Asn Ala Gly Ala
65 70 75 80

Asn Asp Pro Ser Lys Asn Asp Pro Ser Lys Ser Gln Ala Pro Gln Ser
85 90 95

Ala Asn Lys Thr Gly Asn Val Asp Asp Ala Asn Asn Gln Asp Pro Met
100 105 110

Gln Ala Leu Met Gln Leu Leu Glu Asp Leu Val Lys Leu Leu Lys Ala
115 120 125

Ala Leu His Met Gln Gln Pro Gly Gly Asn Asp Lys Gly Asn Gly Val
130 135 140

Gly Gly Ala Asn Gly Ala Lys Gly Ala Gly Gly Gln Gly Gly Leu Ala
145 150 155 160

Glu Ala Leu Gln Glu Ile Glu Gln Ile Leu Ala Gln Leu Gly Gly Gly
165 170 175

Gly Ala Gly Ala Gly Gly Ala Gly Gly Gly Val Gly Gly Ala Gly Gly
180 185 190

Ala Asp Gly Gly Ser Gly Ala Gly Gly Ala Gly Gly Ala Asn Gly Ala
195 200 205

Asp Gly Gly Asn Gly Val Asn Gly Asn Gln Ala Asn Gly Pro Gln Asn
210 215 220

Ala Gly Asp Val Asn Gly Ala Asn Gly Ala Asp Asp Gly Ser Glu Asp
225 230 235 240

Gln Gly Gly Leu Thr Gly Val Leu Gln Lys Leu Met Lys Ile Leu Asn
245 250 255

Ala Leu Val Gln Met Met Gln Gln Gly Gly Leu Gly Gly Gly Asn Gln
260 265 270

Ala Gln Gly Gly Ser Lys Gly Ala Gly Asn Ala Ser Pro Ala Ser Gly
275 280 285

Ala Asn Pro Gly Ala Asn Gln Pro Gly Ser Ala Asp Asp Gln Ser Ser
290 295 300

Gly Gln Asn Asn Leu Gln Ser Gln Ile Met Asp Val Val Lys Glu Val
305 310 315 320

Val Gln Ile Leu Gln Gln Met Leu Ala Ala Gln Asn Gly Gly Ser Gln
325 330 335

Gln Ser Thr Ser Thr Gln Pro Met
340

It is encoded by a DNA molecule having a nucleotide sequence corresponding SEQ. ID. No. 8 as follows:

ATGTCAGTCG GAAACATCCA GAGCCCGTCG AACCTCCCGG GTCTGCAGAA CCTGAACCTC 60

AACACCAACA CCAACAGCCA GCAATCGGGC CAGTCCGTGC AAGACCTGAT CAAGCAGGTC 120

GAGAAGGACA TCCTCAACAT CATCGCAGCC CTCGTGCAGA AGGCCGCACA GTCGGCGGGC 180

GGCAACACCG GTAACACCGG CAACGCGCCG GCGAAGGACG GCAATGCCAA CGCGGGCGCC 240

AACGACCCGA GCAAGAACGA CCCGAGCAAG AGCCAGGCTC CGCAGTCGGC CAACAAGACC 300

GGCAACGTCG ACGACGCCAA CAACCAGGAT CCGATGCAAG CGCTGATGCA GCTGCTGGAA 360

GACCTGGTGA AGCTGCTGAA GGCGGCCCTG CACATGCAGC AGCCCGGCGG CAATGACAAG 420

GGCAACGGCG TGGGCGGTGC CAACGGCGCC AAGGGTGCCG GCGGCCAGGG CGGCCTGGCC 480

-continued

| | | | | | | |
|---|---|---|---|---|---|---|
| GAAGCGCTGC | AGGAGATCGA | GCAGATCCTC | GCCCAGCTCG | GCGGCGGCGG | TGCTGGCGCC | 540 |
| GGCGGCGCGG | GTGGCGGTGT | CGGCGGTGCT | GGTGGCGCGG | ATGGCGGCTC | CGGTGCGGGT | 600 |
| GGCGCAGGCG | GTGCGAACGG | CGCCGACGGC | GGCAATGGCG | TGAACGGCAA | CCAGGCGAAC | 660 |
| GGCCCGCAGA | ACGCAGGCGA | TGTCAACGGT | GCCAACGGCG | CGGATGACGG | CAGCGAAGAC | 720 |
| CAGGGCGGCC | TCACCGGCGT | GCTGCAAAAG | CTGATGAAGA | TCCTGAACGC | GCTGGTGCAG | 780 |
| ATGATGCAGC | AAGGCGGCCT | CGGCGGCGGC | AACCAGGCGC | AGGGCGGCTC | GAAGGGTGCC | 840 |
| GGCAACGCCT | CGCCGGCTTC | CGGCGCGAAC | CCGGGCGCGA | ACCAGCCCGG | TTCGGCGGAT | 900 |
| GATCAATCGT | CCGGCCAGAA | CAATCTGCAA | TCCCAGATCA | TGGATGTGGT | GAAGGAGGTC | 960 |
| GTCCAGATCC | TGCAGCAGAT | GCTGGCGGCG | CAGAACGGCG | GCAGCCAGCA | GTCCACCTCG | 1020 |
| ACGCAGCCGA | TGTAA | | | | | 1035 |

Further information regarding the hypersensitive response elicitor polypeptide or protein derived from *Pseudomonas solanacearum* is set forth in Arlat, M., F. Van Gijsegem, J. C. Huet, J. C. Pemollet, and C. A. Boucher, "PopA1, a Protein which Induces a Hypersensitive-like Response in Specific Petunia Genotypes, is Secreted via the Hrp Pathway of *Pseudomonas solanacearum,*" *EMBO J.* 13:543–533 (1994), which is hereby incorporated by reference.

The hypersensitive response elicitor polypeptide or protein from *Xanthomonas campestris* pv. glycines has an amino acid sequence corresponding to SEQ. ID. No. 9 as follows:

```
Thr Leu Ile Glu Leu Met Ile Val Val Ala Ile Ile Ala Ile Leu Ala
1               5                   10                  15

Ala Ile Ala Leu Pro Ala Tyr Gln Asp Tyr
            20                  25
```

This sequence is an amino terminal sequence having only 26 residues from the hypersensitive response elicitor polypeptide or protein of *Xanthomonas campestris* pv. glycines. It matches with fimbrial subunit proteins determined in other *Xanthomonas campestris* pathovars.

The hypersensitive response elicitor polypeptide or protein from *Xanthomonas campestris* pv. pelargonii is heat stable, protease sensitive, and has a molecular weight of 20 kDa. It includes an amino acid sequence corresponding to SEQ. ID. No. 10 as follows:

```
Ser Ser Gln Gln Ser Pro Ser Ala Gly Ser Glu Gln Gln Leu Asp Gln
1               5                   10                  15

Leu Leu Ala Met
            20
```

Isolation of *Erwinia carotovora* hypersensitive response elictor protein or polypeptide is described in Cui et al., "The RsmA Mutants of *Erwinia carotovora* subsp. carotovora Strain Ecc71 Overexpress hrp $N_{Ecc}$ and Elicit a Hypersensitive Reaction-like Response in Tobacco Leaves," *MPMI,* 9(7):565–73 (1996), which is hereby incorporated by reference. The hypersensitive response elicitor protein or polypeptide is shown in Ahmad et al., "Harpin is Not Necessary for the Pathogenicity of *Erwinia stewartii* on Maize," *8th Int'l. Cong. Molec. Plant-Microbe Interact.,* Jul. 14–19, 1996 and Ahmad, et al., "Harpin is Not Necessary for the Pathogenicity of *Erwinia stewartii* on Maize," *Ann. Mtg. Am. Phytopath. Soc.,* Jul. 27–31, 1996, which are hereby incorporated by reference.

Hypersensitive response elicitor proteins or polypeptides from *Phytophthora parasitica, Phytophthora cryptogea, Phytophthora cinnamoni, Phytophthora capsici, Phytophthora megasperma,* and *Phytophora citrophthora* are described in Kaman, et al., "Extracellular Protein Elicitors from Phytophthora: Most Specificity and Induction of Resistance to Bacterial and Fungal Phytopathogens," *Molec. Plant-Microbe Interact.,* 6(1):15–25 (1993), Ricci et al., "Structure and Activity of Proteins from Pathogenic Fungi Phytophthora Eliciting Necrosis and Acquired Resistance in Tobacco," *Eur. J. Biochem.,* 183:555–63 (1989), Ricci et al., "Differential Production of Parasiticein, and Elicitor of Necrosis and Resistance in Tobacco, by Isolates of *Phytophthora parasitica,*" *Plant Path.* 41:298–307 (1992), Baillreul et al, "A New Elicitor of the Hypersensitive Response in Tobacco: A Fungal Glycoprotein Elicits Cell Death, Expression of Defence Genes, Production of Salicylic Acid, and Induction of Systemic Acquired Resistance," *Plant J.,* 8(4):551–60 (1995), and Bonnet et al., "Acquired Resistance Triggered by Elicitors in Tobacco and Other Plants," *Eur. J. Plant Path.,* 102:181–92 (1996), which are hereby incorporated by reference.

The above elicitors are exemplary. Other elicitors can be identified by growing fungi or bacteria that elicit a hypersensitive response under which genes encoding an elicitor are expressed. Cell-free preparations from culture supernatants can be tested for elicitor activity (i.e. local necrosis) by using them to infiltrate appropriate plant tissues.

Fragments of the above hypersensitive response elicitor polypeptides or proteins as well as fragments of full length elicitors from other pathogens are encompassed by the method of the present invention.

Suitable fragments can be produced by several means. In the first, subclones of the gene encoding a known elicitor protein are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for increase and expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

An example of a useful fragment is the popA1 fragment of the hypersensitive response elicitor polypeptide or protein from *Pseudomonas solanacearum.* See Arlat, M., F. Van Gijsegem, J. C. Huet, J. C. Pemollet, and C. A. Boucher, "PopA1, a Protein Which Induces a Hypersensitive-like Response in Specific Petunia Genotypes is Secreted via the Hrp Pathway of *Pseudomonas solanacearum," EMBO J.* 13:543–53 (1994), which is hereby incorporated by reference. As to *Erwinia amylovora,* a suitable fragment can be, for example, either or both the polypeptide extending between and including amino acids 1 and 98 of SEQ. ID. NO. 3 and the polypeptide extending between and including amino acids 137 and 204 of SEQ. ID. No. 3.

Variants may also (or alternatively) be modified by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The protein or polypeptide of the present invention is preferably produced in purified form (preferably at least about 60%, more preferably 80%, pure) by conventional techniques. Typically, the protein or polypeptide of the present invention is produced but not secreted into the growth medium of recombinant host cells. Alternatively, the protein or polypeptide of the present invention is secreted into growth medium. In the case of unsecreted protein, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to heat treatment and the hypersensitive response elicitor is separated by centrifugation. The supernatant fraction containing the polypeptide or protein of the present invention is subjected to gel filtration in an appropriately sized dextran or polyacrylamide column to separate the proteins. If necessary, the protein fraction may be further purified by ion exchange or HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, PGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli,* its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The method of the present invention can be utilized to treat a wide variety of plants or their seeds to control insects. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana,* Saintpaulia, petunia, pelargonium, poinsettia, chrysanthemum, carnation, and zinnia.

The present invention is effective against a wide variety of insects. For purposes of the present invention, insects (*Phylum Arthropoda,* Class Insecta) also encompasses *Phylum Mollusca* (snails and slugs represented by the spotted garden slug, banded slug, marsh slug, and gray garden slug), Class Arachnida (mites), and *Phylum Nematoda* (roundworms or nematodes). The host range for some of these pests is extensive. For example, the European corn borer is a major pest of corn (dent and sweet corn) but also feeds on over 200 plants species including green, wax, and lima beans and edible soybeans, peppers, potato, and tomato plus many weed species. Additional insect larvae and adult feeding pests which feed on and damage a wide variety of vegetables and small fruits include the following: Vegetables—seed corn maggot, rice armyworm, alfalfa leafhopper, aster leafhopper, beet armyworm, cabbage looper, cabbage root maggot, Colorado potato beetle, corn earworm, cotton or melon aphid, diamondback moth, fall armyworm, flea beetles (various adult species feed on cabbage, mustard, and other crucifiers, cucumber, eggplant, tobacco, potato, melon, and spinach), green peach aphid, onion maggot, onion thrips, pepper maggot, pickleworm (melon worm), potato leafhopper, potato stem borer, potato and corn stalk borer, striped cucumber beetle, spotted cucumber beetle, northern and western corn root worm, thrips, tarnish plant bug, tobacco aphid, tomato pinworm, tomato mole cricket, and rootknot nematode; Small fruits—meadow spittlebug, strawberry bud weevil, strawberry root weevil, tarnish plant bug, and strawberry spider mites; Grapes—grape berry moth, grape cane gallmaker, climbing cutworms, grape leafhoppers (three species), and grape canc girdler. Collectively this group of insects and allied species represents the most economically important group of pests for vegetables, small fruit, and grape production worldwide.

The method of the present invention involving application of the hypersensitive response elicitor polypeptide or protein can be carried out through a variety of procedures when all or part of the plant is treated, including leaves, stems, roots, etc. This may (but need not) involve infiltration of the hypersensitive response elicitor polypeptide or protein into the plant. Suitable application methods include high or low pressure spraying, injection, dusting, and leaf abrasion proximate to when elicitor application takes place. When treating plant seeds, in accordance with the application embodiment of the present invention, the hypersensitive response elicitor protein or polypeptide can be applied by low or high pressure spraying, coating, immersion, dusting, or injection. Other suitable application procedures can be envisioned by those skilled in the art provided they are able to effect contact of the hypersensitive response elicitor polypeptide or protein with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to control insects on the plants. Such propagated plants may, in turn, be useful in producing seeds or propagules (e.g., cuttings) that produce plants capable of insect control.

The hypersensitive response elicitor polypeptide or protein can be applied to plants or plant seeds in accordance with the present invention alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. In this embodiment, the composition contains greater than 500 nM hypersensitive response elicitor polypeptide or protein.

Although not required, this composition may contain additional additives including fertilizer, insecticide, fungicide, nematacide, herbicide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor polypeptide or protein can be applied to plant seeds with other conventional seed formulation and treatment materials, including clays and polysaccharides.

In the alternative embodiment of the present invention involving the use of transgenic plants and transgenic seeds, a hypersensitive response elicitor polypeptide or protein need not be applied topically to the plants or seeds. Instead, transgenic plants transformed with a DNA molecule encoding a hypersensitive response elicitor polypeptide or protein are produced according to procedures well known in the art, such as by biolistics or Agrobacterium mediated transformation. Examples of suitable hypersensitive response elicitor polypeptides or proteins and the nucleic acid sequences for their encoding DNA are disclosed supra. Once transgenic plants of this type are produced, the plants themselves can be cultivated in accordance with conventional procedure with the presence of the gene encoding the hypersensitive response elicitor resulting in control of insects on the plant. Alternatively, transgenic seeds are recovered from the transgenic plants. These seeds can then be planted in the soil and cultivated using conventional procedures to produce transgenic plants. The transgenic plants are propagated from the planted transgenic seeds under conditions effective to control insects. While not wishing to be bound by theory, such growth enhancement may be RNA mediated or may result from expression of the elicitor polypeptide or protein.

When transgenic plants and plant seeds are used in accordance with the present invention, they additionally can be treated with the same materials as are used to treat the plants and seeds to which a hypersensitive response elicitor polypeptide or protein is applied. These other materials, including hypersensitive response elicitors, can be applied to the transgenic plants and plant seeds by the above-noted procedures, including high or low pressure spraying, injection, coating, dusting, and immersion. Similarly, after plants have been propagated from the transgenic plant seeds, the plants may be treated with one or more applications of the hypersensitive response elicitor to control insects. Such plants may also be treated with conventional plant treatment agents (e.g., insecticides, fertilizers, etc.). The transgenic plants of the present invention are useful in producing seeds or propagules (e.g., cuttings) from which plants capable of insect control would be produced.

EXAMPLES

Example 1

Controlling the Spread of Aphids From Colonized or Infested Tobacco

Two to three lower leaves (at position 4) of a tobacco plant were infiltrated with hypersensitive response elicitor at a concentration of 20 μm/ml. Another tobacco plant infiltrated with 5 mM potassium phosphate buffer was used as a control. Any visible aphids on these two plants were then killed. The two plants were placed on a lab bench with a light on at night. Five days after infiltration of hypersensitive response elicitor, a heavily aphid-infected tobacco plant was moved from the greenhouse to the lab bench. The aphid-infected plant was placed close to and between the hypersensitive response elicitor-treated plant and the buffer-infiltrated plant with many of the leaves of the uninfected plants overlapping with those of the infected plant to facilitate movement of the aphids from the infected plant. The number of aphids on hypersensitive response elicitor- and buffer-treated plants were counted once everyday for about 10 days. The result is shown in Table 1.

TABLE 1

Harpin Induced Tobacco Resistance To Aphid Infection

| A Leaf | B Day 1 | | C Day 2 | | D Day 3 | | E Day 6 | | F Day 7 | | G Day 8 | | H Day 9 | | I Day 10 | |
|---|---|---|---|---|---|---|---|---|---|---|---|---|---|---|---|---|
| Position | H | C | H | C | H | C | H | C | H | C | H | C | H | C | H | C |
| 1 | 7 | 5 | 17 | 9 | 8 | 7 | 8 | 9 | 7 | 11 | 4 | 13 | 10 | 22 | 17 | 32 |
| 2 | 3 | 7 | 12 | 5 | 12 | 19 | 8 | 12 | 24 | 39 | 22 | 39 | 17 | 26 | 4 | 22 |
| 3 | 3 | 7 | 3 | 12 | 3 | 27 | 1 | >50 | 4 | >50 | 12 | >50 | 2 | >50 | 4 | >50 |

TABLE 1-continued

Harpin Induced Tobacco Resistance To Aphid Infection

| A Leaf | B Day 1 | | C Day 2 | | D Day 3 | | E Day 6 | | F Day 7 | | G Day 8 | | H Day 9 | | I Day 10 | |
|---|---|---|---|---|---|---|---|---|---|---|---|---|---|---|---|---|
| Position | H | C | H | C | H | C | H | C | H | C | H | C | H | C | H | C |
| 4 | 4 | 10 | 3 | 12 | 2 | >50 | 1 | >50 | 0 | >50 | 0 | >50 | 0 | >50 | 0 | >50 |
| 5 | 2 | 6 | 1 | 8 | 0 | 10 | 0 | 18 | 0 | 22 | 0 | 22 | 0 | 22 | 0 | 26 |
| 6 | 2 | 0 | 2 | 4 | 0 | 4 | 0 | 11 | 0 | 22 | 0 | 20 | 0 | 18 | 1 | 26 |
| 7 | 0 | 0 | 0 | 0 | 0 | 4 | 0 | 14 | 0 | 14 | 2 | 14 | 0 | 10 | 0 | 10 |
| 8 | 1 | 12 | 1 | 4 | 0 | 8 | 1 | 24 | 0 | 22 | 0 | 22 | 0 | 32 | 0 | 32 |
| 9 | 0 | 0 | 0 | 5 | 0 | 5 | 0 | 7 | 0 | 12 | 0 | 9 | 0 | 9 | 0 | 7 |
| 10 | 0 | 0 | 0 | 3 | 0 | 3 | 0 | 13 | 0 | 15 | 0 | 15 | 0 | 12 | 0 | 10 |
| 11 | 0 | 0 | 0 | 5 | 0 | 5 | 0 | 6 | 0 | 11 | 0 | 11 | 0 | 11 | 0 | 19 |
| 12 | 0 | 2 | 0 | 3 | 0 | 11 | 0 | 11 | 0 | 6 | 0 | 6 | 0 | 8 | 0 | 8 |
| 13 | 0 | 0 | 0 | 0 | 0 | 0 | 0 | 2 | 0 | 2 | 0 | 6 | 0 | 6 | 0 | 11 |
| 14 | 0 | 0 | 0 | 0 | 0 | 0 | 0 | 1 | 0 | 6 | 0 | 8 | 0 | 21 | 0 | 14 |
| 15 | 0 | 0 | 0 | 0 | 0 | 7 | 0 | 9 | 0 | 32 | 0 | 32 | 0 | 32 | 0 | 22 |
| 16 | 0 | 0 | 0 | 0 | 0 | 0 | 1 | 0 | 0 | 0 | 0 | 2 | 0 | 4 | 0 | 11 |
| 17 | 0 | 0 | 0 | 0 | 0 | 1 | 0 | 5 | 0 | 5 | 0 | 4 | 0 | 24 | 4 | 22 |
| 18 | 0 | 0 | 2 | 0 | 0 | 0 | 0 | 1 | 0 | 1 | 0 | 1 | 0 | 18 | 0 | 16 |
| 19 | 1 | 11 | 1 | 11 | 0 | 8 | 4 | 17 | 4 | 17 | 0 | 17 | 2 | 13 | 0 | 7 |
| 20 | 0 | 0 | 0 | 0 | 0 | 0 | 0 | 0 | 0 | 0 | 0 | 0 | 4 | 6 | 4 | 14 |
| Total | 23 | 60 | 42 | 81 | 25 | >169 | 24 | >260 | 39 | >337 | 38 | >341 | 37 | >388 | 34 | >409 |

H: Harpin-induced plant
C: Control plant

From these results, it is clear that the hypersensitive response elicitor-treated plant has many fewer aphids than the buffer-treated control plant, suggesting that the aphids did not like to colonize on the hypersensitive response elicitor-treated plants. At the lower three leaves, there was a substantial number of aphids even in the hypersensitive response elicitor-treated plant. Since infiltration of hypersensitive response elicitor started from leaf 4, this indicates that the hypersensitive response elicitor-generated signal for insect-resistance can only effectively travel upward to the top of the tobacco plant.

It was also observed that aphids died 2 days after they moved to the hypersensitive response elicitor-treated plant.

Example 2

Colonization of Aphids in Hypersensitive Response Elicitor-Treated Tobacco Plants From Example 1, it was observed that there were many dead aphids on the hypersensitive response elicitor-treated tobacco leaves. To further confirm this observation, aphids were artificially inoculated on a hypersensitive response elicitor-treated tobacco plant. The number of living and dead aphids were counted once every day for 4 days.

Hypersensitive Response Elicitor Treatment and Aphid Inoculation: Two lower leaves of tobacco plants were infiltrated with hypersensitive response elicitor at a concentration of 20 μg/ml. After 24 hours, tissue necrosis was observed. Seven days after hypersensitive response elicitor infiltration, aphids from an infested (or colonized) plant were transferred to the three upper leaves of the hypersensitive response elicitor-treated plant.

Table 2 summarizes the results of this example. It shows that, after two days, most of the inoculated aphids were dead and some of them moved away from the hypersensitive response elicitor-treated plant; however, the number of the inoculated aphids in the control plant remained about the same.

TABLE 2

Number of Colonized Aphids in Control and Harpin-Treated Tobacco Plants

| A | B Day 0 | | C Day 1 | | D Day 2 | | E Day 3 | | F Day 4 | |
|---|---|---|---|---|---|---|---|---|---|---|
| Leaf | H | C | H | C | H | C | H | C | H | C |
| 1 | 23 | 22 | 18 | 20 | 6 | 20 | 0 | 19 | 0 | 21 |
| 2 | 26 | 27 | 14 | 27 | 3 | 25 | 0 | 25 | 0 | 28 |
| 3 | 31 | 25 | 12 | 26 | 2 | 22 | 1 | 24 | 0 | 20 |
| Total | 80 | 74 | 44 | 73 | 11 | 67 | 1 | 68 | 0 | 69 |

The numbers in the table are live aphids
H: Harpin-induced plant
C: Control plant

Example 3

Tobacco Seedlings Generated from Harpin-Soaked Seeds are Resistant to Aphid Infection About 80 tobacco seeds (*Nicotiana tabacum* L. 'Xanthi') were soaked in harpin solution (about 25 μg/ml of 5 mM potassium phosphate buffer, pH 6.5) for about 16 hours. Then, the harpin-soaked seeds were sowed in a 6" pot with artificial soil. The same treatment using a 5 mM potassium phosphate buffer without harpin was used as a control. The pots were incubated in a growth chamber at a temperature of 25° C. with 14 hour day light. Twenty days after sowing, the size of the tobacco seedlings treated with harpin was significantly greater than that of control plants. Twenty seedlings subjected to each treatment were transplanted to 8" pots 28 days after sowing. The seedlings were then incubated in a growth room at a temperature of about 23° C. using 14 hour day lights. By the time the seedlings were transplanted, aphid infection was observed in the control tobacco seedlings, but not in the harpin-treated seedlings. The source of aphid infection was previously infected adult tobacco plants in the same growth chamber. In the growth room, 7 precolonized adult tobacco plants were placed around the seedlings being tested to serve as a natural source of aphids. Seven days after the seedlings were transplanted, the number of aphids in each tobacco seedlings was counted. As shown in Table 3, 17 out of 20 control plants were infected by aphids with the number of aphids varying between 1 to 13. However, only 2 out of 20 harpin-treated plants were infected by the aphids. This indicates that tobacco plants from harpin-treated seeds are far more resistant to the aphid infection than control plants.

TABLE 3

Tobacco Plants Generated From Harpin-Soaked Seeds Are Resistant To Aphid Infection

| Control | | Harpin-Treated | |
|---|---|---|---|
| Plant No. | Number of Aphids | Plant No. | Number of Aphids |
| 1 | 4 | 1 | 0 |
| 2 | 2 | 2 | 10 |
| 3 | 11 | 3 | 0 |
| 4 | 11 | 4 | 0 |
| 5 | 4 | 5 | 0 |
| 6 | 13 | 6 | 0 |
| 7 | 3 | 7 | 0 |
| 8 | 5 | 8 | 0 |
| 9 | 11 | 9 | 0 |
| 10 | 1 | 10 | 0 |
| 11 | 3 | 11 | 0 |
| 12 | 4 | 12 | 0 |
| 13 | 4 | 13 | 0 |
| 14 | 0 | 14 | 0 |
| 15 | 12 | 15 | 0 |
| 16 | 2 | 16 | 0 |
| 17 | 0 | 17 | 0 |
| 18 | 2 | 18 | 0 |
| 19 | 0 | 19 | 0 |
| 20 | 2 | 20 | 0 |
| Total | 94 | | 10 |

Example 4

Field Study Regarding The Effect Of Hypersensitive Response Elicitor Application On Insect Control An experiment was conducted at the Homer C. Thompson Vegetable Research Farm located in Freeville, N.Y. The experimental design was a randomized complete block with four replications, with 8 plants per rep, using single rows on plastic, with 22 inch spacing between plants. A single inoculated spreader row of peppers ran the length of the plot between the two treatment rows to provide inoculum for the target disease of bacterial leaf spot of pepper (*Xanthomonas campestris* pv. vesicatoria, pepper race). See FIG. 1 . Upwind and across the road from the pepper trial was a commercial field of dent corn which provided a natural source of European corn borer during the season. The pepper variety "Jupiter" was selected because of its strong susceptibility to bacterial leaf spot. Pepper seedlings were transplanted to the field on day 0. Bacterial inoculum was introduced into the plot by two means. Previously infected "Jupiter" seedlings were transplanted to the spreader row on day 26 and the spreader row was additionally inoculated on day 38 with *Xanthomonas campestris* pv. vesicatoria pepper race in order to provided more disease pressure for the peppers rows on either side.

The first application of hypersensitive response elicitor or harpin was made on day 23, before any inoculum was introduced or spread had occurred. A total of four treatments were tested: (1) water sprayed control; (2) Kocide at 3 lb/A; (3) Kocide at 1 lb+Manex fungicide at 1.2 qt/A; and (4) Harpin. The copper fungicide Kocide and the Kocide+Manex (maneb) fungicide are standard materials recommended for bacterial leaf spot control in pepper. Kocide is manufactured by Griffin Corp., Valdosta, Ga., while Manex is produced by Crystal Chemical Inter-Americal, Houston, Tex. All treatments were applied with a $CO_2$ pressurized boom sprayer at approximately 40 psi with 21.5 gal/A being delivered through four TeeJet XR 11003 flat fan nozzles spaced 20 inches apart. This provided excellent foliar coverage. Following initial harpin treatment, all treatments were applied weekly until the experiment was concluded. No additional pesticides, including insecticides, were applied. The first appearance of disease in the test plants was on day 54. Two pepper harvests were made on day 61 and day 97. Data taken included the incidence (i.e. number of plants infected with bacterial leaf spot) per treatment, total number and weight of fruit harvested by category (large, medium, small, and unmarketable), and the total number of fruit showing European corn borer damage expressed as frass or unharvestable because of fruit breakdown by bacterial soft rot *Erwinia carotovora* subsp. carotovora. The involvement of European corn borer became evident at about day 50. Consequently, the amount of soft rot for all treatments was recorded at the day 57 and day 97 harvests. Similarly, it became apparent on the day 57 harvest that European corn borer damage could also be assessed by larval feeding (i.e. frass) on pepper fruit. The European corn borer overwinters as the last larval instar, and, in the spring, the larvae pupate. Adults from the multi-generation strain emerge in late May to early June and again in August. If a single generation strain is present, then the emergence will peak in July. However, in some fields of the Northeast, single and multi-generation strains may be present together. Female moths fly into susceptible crops to lay their eggs, and each female may lay up to 500 eggs during its lifespan. After hatching, the tiny borers crawl to protected areas on the plant to feed, which in the case of pepper, is under the calyx attachment of the pod to the stem. They later borer into the pod, allowing bacteria to enter and rapidly multiply in the moist and humid environment within the pod. Bacterial soft rot can destroy the pod in a manner of days. Differences in European corn borer damage and infestations among treatments was recorded at the time of the second harvest. Data were analyzed and significance established by one-way analysis of variance.

Figure 3:
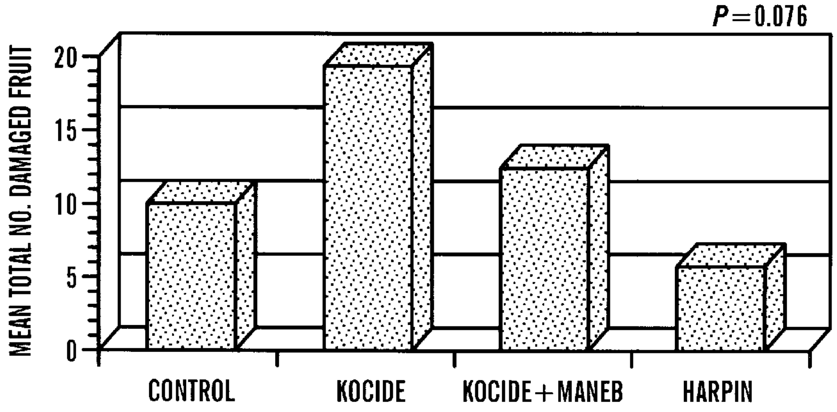
FIG. 3 shows the mean number of pepper fruit (all sizes) damaged by European Corn Borer for control, Kocide, Kocide+Maneb, and hypersensitive response elicitor ("harpin") treatments.
Figure 4:
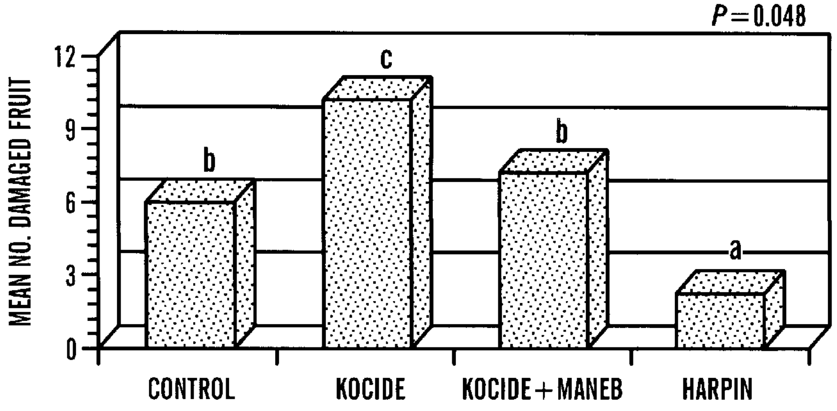
FIG. 4 shows the mean number of large pepper fruit damaged by European Corn Borer for control, Kocide, Kocide+Maneb, and hypersensitive response elicitor ("harpin") treatments.

Bacterial leaf spot foliar infections occurred throughout the plots, but the amount of disease did not allow for any significant differences. Final disease ratings were made on day 97. The harpin treatment provided control equivalent to the commercial treatments of Kocide or Kocide+Manex, and all were better than the water-sprayed control. The number of European corn borer (ECB) damaged fruit that were rotting on the plants on day 97 were recorded; they could not be harvested because of watery collapse. The harpin treated plots had fewer rotting pepper pods, and although not significantly different from the other treatments (P=0.229), the amount of protection provided with the harpin sprays was evident (See FIG. 2). Another indication of the amount of damage caused by European corn borer feeding was the number of fruit showing feeding damage or frass. The harpin treated fruit had substantially less fruit damage across all fruit sizes (P=0.076), when compared with all other treatments (See FIG. 3). The number of large fruit with borer damage was significantly reduced (P=0.048) when sprayed with harpin (See FIG. 4).

The benefit of using harpin to reduce the damage caused by the European corn borer was reflected in two ways. First, substantially less bacterial soft rot leading to loss of fruit in the field was noted when harpin was applied weekly.

Secondly, the number of fruit with direct borer feeding (i.e. frass) was much lower in harpin treated plots than all other treatments. The greatest impact of harpin treatment on economic factors was the greater production of undamaged fruit across all size categories, and the greater yield of healthy large fruit which have the highest dollar value.

Example 5

Control of Aphid from Foliar Application of HP-1000™ Hypersensitive Response Elicitor to Cotton Cotton aphids (*Aphis gossypii*) leave a "honeydew" deposit that contaminates the lint and reduces crop value. A field trial to determine the effect of HP-1000™ Hypersensitive Response Elicitor from *Erwinia amylovora* (Eden Bioscience Corp., Bothell, Wash.) on cotton (var. Acala) was seeded in replicated (4×) plots (3.2×25 feet) in a randomized complete block design. Treatments were HP-1000™ at 20, 60, and 80 μg/ml (a.i.) and a chemical insecticide, Asana XL® (DuPont Agricultural Products, Wilmington, Del.), at 8 oz./ac. Foliar treatments were applied beginning at cotyledon to three true leaves and thereafter at 14 day intervals using a back-pack sprayer. Aphid counts were made immediately prior to spray applications at 14, 28, 35, and 42 days after the first treatment (DAT 1). Twenty-five randomly selected leaves per plot were collected at the first three sampling dates, and ten leaves per plot at the final sampling date.

At 14 DAT 1 (i.e. on day 14), aphid counts were relatively low across all treatments, but by 28 DAT 1 (two sprays applied) (i.e. on day 28) the number of aphids per leaf were significantly greater in Asana XL® treated plots compared to the HP-1000 ™ treated plots (Table 4). By 35 DAT 1 (three sprays applied) (i.e. on day 35), aphid counts had risen for all treatment rates, yet aphid counts per leaf was still significantly lower for HP-1000™ treated cotton compared to the Asana XL® treatment. Finally, at 42 DAT 1 (four sprays applied) (i.e. on day 42), the number of aphids per leaf had increased to a level that threatened to overwhelm all treatments, including the chemical standard insecticide. At this point, Pravado™ aphicide (Bayer Corporation, Agricultural Division, Kansas City, Mo.) was applied to all plots to eradicate aphids from all treatments and the trial was continued for crop yield only.

These data indicate that cotton treated with HP-1000™ deterred light to moderate aphid pressure and that this effect was significantly better than a standard chemical insecticide, Asana XL®.

TABLE 4

Aphid Count per Leaf on Cotton After Treatment with Asana XL ® or HP-1000 ™

| | | Number of Aphids Per Leaf[1] No. Sprays Applied/Days After Treatment | | | |
|---|---|---|---|---|---|
| Treatment | Rate[2] | 1/14DAT1 | 2/28DAT1 | 3/35DAT1 | 4/42DAT1 |
| Asana XL ® | 8 oz/ac | 0.2 a | 32.2 a | 110.0 a | 546.9 a |
| HP-1000 ™ | 20 μg/ml | 0.2 a | 7.8 b | 22.9 b | 322.1 a |
| HP-1000 ™ | 60 μg/ml | 0.1 a | 4.9 b | 34.6 b | 168.3 a |
| HP-1000 ™ | 80 μg/ml | 0.0 a | 2.7 b | 25.8 b | 510.2 a |

[1]Means followed by different letters are significantly different according to Duncan's MRT, P = 0.05.
[2]Rate for Asana XL ® is for formulated product, rate for HP-1000 ™ is for active ingredient (a.i.).

Example 6

Control of Strawberry Spider Mites by Foliar Application of HP-1000™ to Cotton Mites cause foliar damage to cotton thus reducing potential crop yield. To assess potential mite control of HP-1000™, cotton (var. Acala) was seeded in replicated (4×) field plots (3.2×25 feet) in a randomized complete block field trial. Treatments included HP-1000™ at 20, 60, and 80 μg/ml and a chemical insecticide for mites, Zephyr® (Novartis, Greensboro, N.C.), at 6 oz./ac. HP-1000™ treatments were applied at 14 day intervals using a back-pack sprayer beginning when the crop was at three true leaves. Zephyr® was applied once, on the same date as the first application of HP-1000™. A pretreatment evaluation for strawberry spider mites (*Tetranychus turkestani*) was made immediately before the first spray and again at 4, 7, 14, and 28 days after the first treatment (DAT 1).

Mite populations were determined by collecting twenty-five randomly chosen cotton leaves per plot. All leaves were brushed with a mite brushing machine and dislodged mites were uniformly distributed onto a rotating glass plate, pretreated with a wetting agent to which they adhered. The number of motile adult mites were counted under a 30× binocular microscope. This figure was then converted to a per leaf unit.

A count of living or motile adult mites per leaf at the five assessment times did not appear to show significant treatment effects at any of the evaluation times (Table 5).

TABLE 5

Number of Adult Motile Mites per Leaf After Treatment with Zephyr ® or HP-1000 ™.

| | | Number of motile mites per leaf evaluation timing | | | | |
|---|---|---|---|---|---|---|
| Treatment | Rate[2] | 0DAT1 | 4DAT1 | 7DAT1 | 14DAT1 | 28DAT1 |
| Zephyr ® | 6 oz/ac | 3.4 | 0.2 | 0.4 | 0.0 | 0.0 |
| HP-1000 ™ | 20 μg/ml | 2.0 | 0.6 | 0.3 | 0.0 | 0.0 |
| HP-1000 ™ | 60 μg/ml | 3.7 | 0.5 | 0.1 | 0.2 | 0.1 |
| HP-1000 ™ | 80 μg/ml | 3.0 | 1.4 | 0.4 | 0.0 | 0.0 |

[1]Rate for Zephyr ® is for formulated product, rate for HP-1000 ™ is for active ingredient (a.i.).

However, using the method of Henderson et al., "Tests With Acaracides Against Brown Wheat Mites," *J. Econ. Ent. Vol.* 48(2):157–61 (1955), which is hereby incorporated by refrence ("Henderson"), to calculate percent mortality revealed the mite control was different between treatments. (Table 6).

Henderson's Method is defined as:

$$\text{Percent Mortality} = \frac{Ta \times Cb}{1 - Tb \times Ca} \times 100$$

where;

Ta=Number of motile mites counted after treatment,

Tb=Number of motile mites counted prior to treatment,

Ca=Number of mites in the control (check) after treatment of the test plots, and Cb=Number of mites in the control (check) plot before treatment of the test plots.

When percent mortality was calculated at 4 DAT 1, mite control from treatment with HP-1000™ was over two times greater compared to Zehpyr® (Table 6). By 7 DAT 1, mite control was still substantially better from HP-1000™ treatment than for Zephyr®. At 14 DAT 1, mite control for HP-1000 at 80 μg/ml reached its maximum at just under 84%, roughly comparable to that seen for the Zephyr® treatment. For the remaining 14 days, mite control by HP-1000 treatments tended to decline relative to the Zephyr®. Treatment with Zephyr® reached 100% mite control by 28 DAT 1 (Table 6).

TABLE 6

Control of Motile Adult Mites on Cotton from Treatment with HP-1000 ™ as Measured by Henderson's Method.

| | | Percent control of motile mites[1] evaluation timing | | | |
|---|---|---|---|---|---|
| Treatment | Rate[2] | 4DAT1 | 7DAT1 | 14DAT1 | 28DAT1 |
| HP-1000 ™ | 20 μg/ml | 56.6 | 76.5 | 68.4 | 66.7 |
| HP-1000 ™ | 60 μg/ml | 57.1 | 50.0 | 78.5 | 40.0 |
| HP-1000 ™ | 80 μg/ml | 53.6 | 77.9 | 83.8 | 60.0 |
| Zephyr ® | 6 oz/ac | 28.0 | 66.7 | 89.9 | 100.0 |

[1]Percent control calculated using Henderson's method (1955).
[2]Rate for Zephyr ® is for formulated product, rate for HP-1000 ™ is for active ingredient (a.i.).

These data indicate that the mode of action for mite control is different between HP-1000™ and Zephyr®. Complete control by treatment with Zephyr® was not achieved until 28 DAT. Weekly treatments with HP-1000198 resulted in relatively "steady" mite control throughout the 28 day evaluation period. This suggests HP-1000™ may trigger an internal insect resistance process fundamentally different than chemical insecticide activity.

Example 7

Reduced Feeding Activity of Mole Cricket in Tomato from Foliar Application of HP-1000™

Fresh market tomatoes (var. Agri-set) were planted at 12-inch spacing in 25 foot rows replicated 5 times in a randomized completed block design field trial. This disease control trial was not specifically designed to assess insect resistance from treatment with HP-1000™. Foliar applications of HP-1000™ at 20 and 40 μg/ml were applied beginning at first true leaves and repeated at 7 day intervals for 8 sprays. Additional treatment included a standard commercial fungicide mixture (Bravo® (Zeneca Ag Products, Wilmington, Del.)+Manex™+Kocide®) for control against bacterial blight disease. After the first four spays were applied, a field evaluation was made to determine and the number of plants damaged (girdled) by feeding of mole cricket (*Scapteriscus vicinus,* scudder). Data presented in Table 7 indicates that HP-1000™ treated plants had considerably less girdling from mole cricket feeding. Continued evaluations of this trial were not possible due to complete crop loss from virus infection.

TABLE 7

Reduced Stem Girdling of Tomatoes by Mole Cricket from Application of HP-1000 ™.

| Treatment | Rate[1] | No. Plant girdled[2] | % chg. Vs. UTC |
|---|---|---|---|
| UTC | — | 15 | — |
| Bravo ® +Manex ™ +Kocide ® | 1 quart/ac 2 lbs/ac 1.5 pints/ac | 12 | −20 |
| HP-1000 ™ | 40 μg/ml | 4 | −73 |
| HP-1000 ™ | 40 μg/ml | 7 | −53 |

[1]Rates for Bravo ®, Manex ® and Kocide ® are for formulated product; rates for HP-1000 are for a.i.
[2]Average number of plants from 50 plants per replicate.

Example 8

Reduced Feeding Activity of Army Worm in Rice from Foliar Application of HP-1000™

Rice seed (var. M-202) was presoaked for 24 hours in a solution of HP-1000™ at a concentration of 20 μg/ml (a.i.). Treated rice was then seeded into randomized (5×) field plots 10×15 feet. An untreated control treatment was also included; no foliar sprays were applied to this trial. Observation at 41 days after planting revealed significant damage to leaves due to feeding of armyworm (*Spodoptera praefica*) larvae. To quantify the damage, one hundred randomly selected tillers were taken from HP-1000™ treated as well as untreated plots. Samples were ranked for damage according to the following scale:

1=no tiller leaves damaged

2=one tiller leaves with feeding damage

3=two tiller leaves with feeding damage

4=three tiller leaves with feeding damage

5=four or all tiller leaves with feeding damage

Results from these rankings were then analyzed for treatment differences. Data presented in Table 8 indicate that rice plants treated with HP-1000™ had significantly less feeding damage than the UTC plants. HP-1000™ treated rice was virtually untouched by armyworm feeding.

TABLE 8

| Reduced Armyworm Feeding on Rice After Seed Soak Treatment with HP-1000 ™. | | |
|---|---|---|
| Treatment | Rate[1] | Median Rating[2] |
| UTC | | 3 (two tiller leaves damaged) |
| HP-1000 ™ | 20 μg/ml | 1 (no tiller leaves damaged) |

[1]Rate is for active ingredient applied (a.i.).
[2]Difference in median values among the two groups is statistically different according to Mann-Whitney Rank Sum Test, P = 0.0001.

Example 9

Reduced Feeding Activity of Aphids in Tobacco from Foliar Application of HP-1000™

Tobacco seedlings were treated with two foliar sprays of HP-1000™ at rates of 15, 30, and 60 μg/ml (a.i.). The first application was made to seedlings, the second approximately 42 days later after transplanting into replicated (3×) field plots. Two days after the second application, counts for tobacco worm and aphid were made. Data presented in Table 9 illustrate that HP-1000™ treatment substantially reduced the amount of feeding activity from both tobacco worm and aphid.

TABLE 9

| Reduced Feeding Activity of Tobacco Worm and Aphid from Treatment with HP-1000 ™ on Tobacco. | | | |
|---|---|---|---|
| Treatment | Rate | No. tobacco worms/100 plants | Percent of plants with aphids feeding |
| UTC | | 20 | 13 |
| HP-1000 ™ | 15 μg/ml | 10 | 7 |
| HP-1000 ™ | 30 μg/ml | 4 | 4 |
| HP-1000 ™ | 60 μg/ml | 10 | 7 |

Example 10

Tomato Seedlings Treated with HP-1000™ Show Tolerance to Nematodes

Tomato seedlings (var. Rutgers) were germinated in flats and grown for four weeks before transplanting into pots, two plants per pot, replicated eight times. At transplanting, seedlings were treated with HP-1000™ at 25 μg/ml via root soaking. one week after transplanting, each pot was inoculated with approximately 10,000 root knot nematode, RKN, (*Meloidogyne hapla*) eggs. Thereafter, weekly root drenches of HP-1000™ continued until four weeks. After four weeks, one plant in each pot was evaluated for root weight and the number of galls (i.e. infections sites on the roots from nematode parasitism). The remaining plants were then treated with four weekly foliar sprays of HP-1000™ (25 μg/ml a.i.). After all treatments had been applied, these plants were then evaluated for root weight, shoot weight, and number of fruit per plant. Four weeks after inoculation, the number of galls per plant was slightly higher for HP-1000™ treated plants than for the control plants, yet the shoot weight was significantly greater for HP-1000™ treated plants (Table 10).

TABLE 10

| Number of Galls and Shoot Weight of RKN-inoculated Tomatoes After Treatment with HP-1000 ™. | | | |
|---|---|---|---|
| Treatment | Rate[1] | No. Galls/plant | Shoot wt.[2] (g/plant) |
| UTC | — | 427 | 32.8 a |
| HP-1000 ™ | 25 μg/ml | 507 | 39.5 b |

[1]Rate is for amount of active ingredient, a.i.
[2]Means followed by different letters are significantly different according to Duncan's MRT, P = 0.05.

This indicated that even though nematodes were infecting HP-1000™ treated plants, plant growth was still enhanced by the HP-1000™ treatment. Eight weeks after inoculation, (four additional foliar HP-1000™ sprays applied) shoot weight was still significantly higher for HP-1000™ treated plants vs. control plants also inoculated with RKN and the average number of fruit per plant was numerically higher in the HP-1000™ treated plants (Table 11).

TABLE 11

| Average Shoot Weight and Average Number of Fruit per Plant of RKN-inoculated Tomatoes After Treatment with HP-1000 ™. | | | |
|---|---|---|---|
| Treatment | Rate[1] | Shoot wt.[2] (g/plant) | No. Fruit/plant |
| UTC | — | 69.9 a | 0.875 |
| HP-1000 ™ | 25 μg/ml | 89.8 b | 1.25 |

[1]Rate is for amount of active ingredient, a.i.
[2]Means followed by different letters are significantly different according to Duncan's MRT, P = 0.05.

These results indicate that treatment with HP-1000™ appears to enable the tomato plants to "tolerate" the negative impact of the nematodes.

Example 11

Effect of *Erwinia amylovora* Hypersensitive Response Elicitor on Repellency of Cucumbers to Striped Cucumber Beetles The hypersensitive response elicitor protein encoded by the hrpN gene of *Erwinia amylovora* ("harpin") was produced by fermentation of the cloned gene in a high-expression vector in *Escherichia coli*. High-pressure liquid chromatography analysis of the cell-free elicitor preparation was used to determine its harpin content. Treatment dilutions were prepared in water. Harpin was applied as a foliar spray to caged, cucumber plants, Marketmore 76, lot #1089, to assess its ability to repel the striped cucumber beetle, *Acalymma vittatum* (Fabricius). Harpin from *E. amylovora* was applied in water at 0, 5, and 10 mg/l to cucumber plants 21-days after sowing seed in the greenhouse (plants had both cotyledons and 6–8 fully expanded leaves/plant). Each concentration was applied to three plants per block, and the treatments were replicated three times. Seven days after treatment, a mean of 4.6 adult beetles per plant were introduced manually. The insects were allowed to feed for 7 days before feeding damage to the plants was evaluated. The number of cotyledons and the number of leaves showing any damage from beetle feeding was determined. A rating scale of 0–6 (where 0=no obvious feeding; 1=<15% damage; 2=<25% damage; 3=<50% damage; 4=>50% damage;

5=>75% damage; and 6=leaf desiccated or dead due to feeding) was used to estimate the extent of damage from beetle feeding on the cotyledons and leaves.

Table 12 summarizes the effect of hypersensitive response elicitor protein concentration on insect damage. The mean percent of damaged cotyledons was in direct proportion to the harpin concentration, whereas the damage to leaves was inversely proportional to harpin concentration.

TABLE 12

Effect of Treating Cucumber Foliage with a Hypersensitive Response Elicitor on the Subsequent Feeding Damage Caused by the Striped Cucumber Beetle (*Acalymma vittatum* [Fabricius]).

| Harpin Concentration (mg/l) | Cotyledons[1] Percent Damaged | Leaves Percent Damaged | Leaves Damage Rating |
|---|---|---|---|
| 0 | 34 | 42 | 5.42 |
| 5 | 50 | 18 | 3.40 |
| 10 | 67 | 5 | 3.20 |

[1]Nine plants per treatment in three blocks of three each. Damage was assessed on a 0–6 scale where 0 = no feeding injury, and 6 = cotyledons and leaves dead because of extensive beetle feeding.

More damage probably occurred on the lower cotyledons, because most of the foliar harpin spray was directed to the upper foliage and it was assumed that more harpin activity would be found in the upper leaves (upward or systemic harpin effect). The cotyledons were thus very attractive for beetle feeding. Less damage occurred on leaves of plants that had been treated with the higher concentration of harpin. Thus, the effectiveness of the treatment on leaves increased as the harpin concentration increased.

The effect of harpin is significant for two reasons: 1) damage from beetle feeding on cucurbits, especially cucumbers, melons, pumpkins, and summer and winter squash, is reduced, because treatment of cucumber with harpin resulted in the plants becoming less attractive (repulsive or repellent) to insect feeding and 2) damage from the bacterial wilt disease is likely to be reduced because these same beetles vector the bacterium responsible for the disease. By preventing feeding, transmission of the bacterium responsible for the disease could be reduced or eliminated. This study shows that harpin may be used to decrease insect damage caused by beetle feeding. Thus, the number of applications of insecticides to particularly insect-sensitive cucurbits might be reduced or eliminated with harpin.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of insect control for plants comprising:

applying a hypersensitive response elicitor polypeptide or protein to a plant or plant seed under conditions effective to control insects on the plant or plants grown from the plant seed.

2. A method according to claim 1, wherein the hypersensitive response elicitor polypeptide or protein corresponds to that obtained from a pathogen selected from the group consisting of Erwinia, Pseudomonas, Xanthomonas, Phytophthora, and mixtures thereof.

3. A method according to claim 2, wherein the hypersensitive response elicitor polypeptide or protein corresponds to that obtained from *Erwinia chrysanthemi*.

4. A method according to claim 2, wherein the hypersensitive response elicitor polypeptide or protein corresponds to that obtained from *Erwinia amylovora*.

5. A method according to claim 2, wherein the hypersensitive response elicitor polypeptide or protein corresponds to that obtained from *Pseudomonas syringae*.

6. A method according to claim 2, wherein the hypersensitive response elicitor polypeptide or protein corresponds to that obtained from *Pseudomonas solanacearum*.

7. A method according to claim 2, wherein the hypersensitive response elicitor polypeptide or protein corresponds to that obtained from *Xanthomonas campestris*.

8. A method according to claim 2, wherein the hypersensitive response elicitor polypeptide or protein corresponds to a Phytophthora species.

9. A method according to claim 1, wherein the plant is selected from the group consisting of dicots and monocots.

10. A method according to claim 9, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

11. A method according to claim 9, wherein the plant is selected from the group consisting of rose, Saintpaulia, petunia, pelargonium, poinsettia, chrysanthemum, carnation, and zinnia.

12. A method according to claim 1, wherein plants are treated by said applying is carried out by spraying, injection, or leaf abrasion at a time proximate to when said applying takes place.

13. A method according to claim 1, wherein plant seeds are treated by said applying which is carried out by spraying, injection, coating, dusting, or immersion.

14. A method according to claim 1, wherein the hypersensitive response elicitor polypeptide or protein is applied to plants or plant seeds as a composition further comprising a carrier.

15. A method according to claim 14, wherein the carrier is selected from the group consisting of water, aqueous solutions, slurries, and powders.

16. A method according to claim 14, wherein the composition contains greater than 0.5 nM of the hypersensitive response elicitor polypeptide or protein.

17. A method according to claim 14, wherein the composition further contains additives selected from the group consisting of fertilizer, insecticide, fungicide, nematacide, and mixtures thereof.

18. A method according to claim 1, wherein the hypersensitive response elicitor polypeptide or protein is in isolated form.

19. A method according to claim 1, wherein the hypersensitive response elicitor polypeptide or protein is provided by bacteria which do not cause disease and are transformed with a gene encoding the hypersensitive response elicitor polypeptide or protein.

20. A method according to claim 1, wherein the hypersensitive response elicitor polypeptide or protein is provided by bacteria which cause disease in some plant species, but not in those subjected to said applying, and contain a gene encoding the hypersensitive response elicitor polypeptide or protein.

21. A method according to claim 1, wherein said applying results in infiltration of the polypeptide or protein into the plant.

22. A method according to claim 1, wherein said applying is effective to prevent insects from contacting plants to which the hypersensitive response elicitor is applied.

23. A method according to claim 22, wherein plants are treated by said applying.

24. A method according to claim 22, wherein plant seeds are treated during said applying, said method further comprising:

planting the seeds treated with the hypersensitive response elicitor in natural or artificial soil and propagating plants from the seeds planted in the soil.

25. A method according to claim 1, wherein said applying is effective to cause insects to depart from plants to which the hypersensitive response elicitor is applied.

26. A method according to claim 25, wherein plants are treated by said applying.

27. A method according to claim 25, wherein plant seeds are treated by said applying, said method further comprising:

planting the seeds treated with the hypersensitive response elicitor in natural or artificial soil and propagating plants from the seeds planted in the soil.

28. A method according to claim 1, wherein said applying is effective to kill insects proximate to plants to which the hypersensitive response elicitor is applied.

29. A method according to claim 28, wherein plants are treated by said applying.

30. A method according to claim 28, wherein plant seeds are treated by said applying, said method further comprising:

planting the seeds treated with the hypersensitive response elicitor in natural or artificial soil and propagating plants from the seeds planted in the soil.

31. A method according to claim 1, wherein said applying is effective to interfere with insect larval feeding on plants to which the hypersensitive response elicitor is applied.

32. A method of insect control for plants comprising:

providing a transgenic plant or plant seed transformed with a DNA molecule encoding a hypersensitive response elicitor polypeptide or protein and growing the transgenic plants or transgenic plants produced from the transgenic plant seeds under conditions effective to control insects.

33. A method according to claim 32, wherein the hypersensitive response elicitor polypeptide or protein corresponds to that obtained from a pathogen selected from the group consisting of Erwinia, Pseudomonas, Xanthomonas, Phytophthora, and mixtures thereof.

34. A method according to claim 33, wherein the hypersensitive response elicitor polypeptide or protein corresponds to that obtained from *Erwinia chrysanthemi.*

35. A method according to claim 33, wherein the hypersensitive response elicitor polypeptide or protein corresponds to that obtained from *Erwinia amylovora.*

36. A method according to claim 33, wherein the hypersensitive response elicitor polypeptide or protein corresponds to that obtained from *Pseudomonas syringae.*

37. A method according to claim 33, wherein the hypersensitive response elicitor polypeptide or protein corresponds to that obtained from *Pseudomonas solanacearum.*

38. A method according to claim 33, wherein the hypersensitive response elicitor polypeptide or protein corresponds to that obtained from *Xanthomonas campestris.*

39. A method according to claim 33, wherein the hypersensitive response elicitor polypeptide or protein corresponds to that obtained from a Phytophthora species.

40. A method according to claim 32, wherein the plant is selected from the group consisting of dicots and monocots.

41. A method according to claim 40, wherein the plant is selected from the group consisting of alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane.

42. A method according to claim 40, wherein the plant is selected from the group consisting of rose, Saintpaulia, petunia, pelargonium, poinsettia, chrysanthemum, carnation, and zinnia.

43. A method according to claim 32, wherein a transgenic plant is provided.

44. A method according to claim 32, wherein a transgenic plant seed is provided.

45. A method according to claim 32, further comprising:

applying the hypersensitive response elicitor polypeptide or protein to the propagated plants to further effect insect control.

46. A method according to claim 32, wherein said insect control prevents insects from contacting plants.

47. A method according to claim 32, wherein said insect control causes insects to depart from transgenic plants.

48. A method according to claim 32, wherein said insect control kills insects.

49. A method according to claim 32, wherein said insect control interferes with insect larval feeding on plants.

* * * * *